United States Patent
Perez-Leal

(10) Patent No.: US 10,883,120 B2
(45) Date of Patent: Jan. 5, 2021

(54) DNA PLASMIDS FOR THE FAST GENERATION OF HOMOLOGOUS RECOMBINATION VECTORS FOR CELL LINE DEVELOPMENT

(71) Applicant: Temple University-Of The Commonwealth System of Higher Education, Philadelphia, PA (US)

(72) Inventor: Oscar M. Perez-Leal, Atlantico Barranquilla (CO)

(73) Assignee: Temple University-Of The Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 16/568,771

(22) Filed: Sep. 12, 2019

(65) Prior Publication Data
US 2020/0002729 A1 Jan. 2, 2020

Related U.S. Application Data

(63) Continuation of application No. 16/346,614, filed as application No. PCT/US2017/059816 on Nov. 3, 2017.

(60) Provisional application No. 62/416,802, filed on Nov. 3, 2016.

(51) Int. Cl.
| | |
|---|---|
| *C12N 15/90* | (2006.01) |
| *C12N 5/07* | (2010.01) |
| *C12N 5/16* | (2006.01) |
| *C12N 15/85* | (2006.01) |

(52) U.S. Cl.
CPC ............ *C12N 15/907* (2013.01); *C12N 5/06* (2013.01); *C12N 5/16* (2013.01); *C12N 15/85* (2013.01); *C12N 2310/20* (2017.05); *C12N 2800/80* (2013.01)

(58) Field of Classification Search
CPC ........ C12N 15/907; C12N 15/85; C12N 5/06; C12N 5/16; C12N 2310/20; C12N 2800/80
USPC ....................................................... 435/320.1
See application file for complete search history.

(56) References Cited

U.S. PATENT DOCUMENTS

| | | | |
|---|---|---|---|
| 2002/0004242 A1 | 1/2002 | McVey | |
| 2009/0111099 A1 | 4/2009 | Ma | |
| 2013/0117870 A1 | 5/2013 | Fahrenkrug | |
| 2016/0186168 A1 | 6/2016 | Konieczka | |

OTHER PUBLICATIONS

System Biosciences PrecisionXTM HR Targeting Vectors User Manual, 2014, Version 16-122914, pp. 1-67.*
Perkel (2012) Life Science Articles:Editorial Articels—"Protein Tagging Technologies: New Ways to Tag and Track Your Protein". https://www.biocompare.com/Editorial-Articles/41670-Protein-Tagging-Technologies/, pp. 1-7.*
Lund et al. (2014) Microbial Cell Factories, vol. 13(38), pp. 1-7.*
Cui et al. (2015) Sci. Rep. vol. 5, 10482; doi: 10.1038/srep10482, pp. 1-11.*
Kimura et al., Scientific Reports, 2015, vol. 5:10710, pp. 1-11.

* cited by examiner

*Primary Examiner* — Anne Marie S Wehbe
(74) *Attorney, Agent, or Firm* — Riverside Law LLP

(57) ABSTRACT

The present invention provides homologous recombination vectors to insert transgenic DNA in cells. These vectors shorten the production time and allow for easy generation of genetically modified cells. The invention allows the user to test multiple tags and to generate homozygous modified cell line using the homologous recombination vector. The invention can be used to generate knockout cells, to generate cell lines with knockin genes, to generate cell lines for drug screening against any target, to create transgenic animals, or in gene therapy.

1 Claim, 13 Drawing Sheets
Specification includes a Sequence Listing.

A.

B.

Histone 3- mRuby3
Nuclear fluorescence

Fig. 9A-9C

SEQUENCE LISTING

```
<160> NUMBER OF SEQ ID NOS: 2

<210> SEQ ID NO 1
<211> LENGTH: 1802
<212> TYPE: DNA
<213> ORGANISM: Artificial Sequence
<220> FEATURE:
<223> OTHER INFORMATION: Fast-HDR donor plasmid backbone with linker
      peptide
<220> FEATURE:
<221> NAME/KEY: misc_feature
<222> LOCATION: (706)..(780)
<223> OTHER INFORMATION: n is a, c, g, or t
<220> FEATURE:
<221> NAME/KEY: misc_feature
<222> LOCATION: (859)..(933)
<223> OTHER INFORMATION: n is a, c, g, or t

<400> SEQUENCE: 1
ggtaccggct tactaaaagc cagataacag tatgcgtatt tgcgcgctga ttttgcggt       60 ataagaatat atactgatat gtatacccga agtatgtcaa aaagaggtgt gctatgaagc    120
agcgtattac agtgacagtt gacagcgaca gctatcagtt gctcaaggca tatatgatgt    180
caatatctcc ggtctggtaa gcacaaccat gcagaatgaa gcccgtcgtc tgcgtgccga    240
acgctggaaa gcggaaaatc aggaagggat ggctgaggtc gcccggttta ttgaaatgaa    300
cggctctttt gctgacgaga acaggggactg gtgaaatgca gtttaaggtt tacacctata    360
aaagagagag ccgttatcgt ctgtttgtgg atgtacagag tgatattatt gacacgcccg    420
ggcgacggat ggtgatcccc ctggccagtg cacgtctgct gtcagataaa gtctcccgtg    480
aactttaccc ggtggtgcat atcggggatg aaagctggcg catgatgacc accgatatgg    540
ccagtgtgcc ggtctccgtt atcggggaag aagtggctga tctcagccac cgcgaaaatg    600
acatcaaaaa cgccattaac ctgatgttct ggggaatata aatgtcaggc tccgttatac    660
acagccagtc tgcaggtcga cggtacccaa ggcggtggag aattcnnnnn nnnnnnnnnn    720
nnnnnnnnnn nnnnnnnnnn nnnnnnnnnn nnnnnnnnnn nnnnnnnnnn nnnnnnnnnn    780
gaattcggat ctggagcaac aaacttctca ctactcaaac aagcaggtga cgtggaggag    840
aatcccgggc cttctagann nnnnnnnnnn nnnnnnnnnn nnnnnnnnnn nnnnnnnnnn    900
nnnnnnnnnn nnnnnnnnnn nnnnnnnnnn nnntctagat aaattcgtca gtagggttgt    960
aaaggttttt cttttcctga gaaacaacc ttttgttttc tcaggttttg cttttggcc    1020 tttccctagc ttttaaaaaa aaaagcaaa agacgctggt ggctggcact cctggtttcc    1080
aggacggggt tcaagtccct gcggtgtctt tgcttggatc cggcttacta aaagccagat    1140
aacagtatgc gtatttgcgc gctgattttt gcggtataag aatatatact gatatgtata    1200
cccgaagtat gtcaaaaaga ggtgtgctat gaagcagcgt attacagtga cagttgacag    1260
cgacagctat cagttgctca aggcatatat gatgtcaata tctccggtct ggtaagcaca    1320
accatgcaga atgaagcccg tcgtctgcgt gccgaacgct ggaaagcgga aaatcaggaa    1380
```

```
gggatggctg aggtcgcccg gtttattgaa atgaacggct cttttgctga cgagaacagg    1440
gactggtgaa atgcagttta aggtttacac ctataaaaga gagagccgtt atcgtctgtt    1500
tgtggatgta cagagtgata ttattgacac gcccgggcga cggatggtga tccccctggc    1560
cagtgcacgt ctgctgtcag ataaagtctc ccgtgaactt tacccggtgg tgcatatcgg    1620
ggatgaaagc tggcgcatga tgaccaccga tatggccagt gtgccggtct ccgttatcgg    1680
ggaagaagtg gctgatctca gccaccgcga aaatgacatc aaaaacgcca ttaacctgat    1740
gttctgggga atataaatgt caggctccgt tatacacagc cagtctgcag gtcgacggat    1800
cc                                                                   1802

<210> SEQ ID NO 2
<211> LENGTH: 2227
<212> TYPE: DNA
<213> ORGANISM: Artificial Sequence
<220> FEATURE:
<223> OTHER INFORMATION: Fast-HDR donor plasmid backbone with internal
      promoter
<220> FEATURE:
<221> NAME/KEY: misc_feature
<222> LOCATION: (706)..(755)
<223> OTHER INFORMATION: n is a, c, g, or t
<220> FEATURE:
<221> NAME/KEY: misc_feature
<222> LOCATION: (1309)..(1358)
<223> OTHER INFORMATION: n is a, c, g, or t

<400> SEQUENCE: 2
ggtaccggct tactaaaagc cagataacag tatgcgtatt tgcgcgctga ttttttgcggt    60 ataagaatat atactgatat gtatacccga agtatgtcaa aaagaggtgt gctatgaagc    120
agcgtattac agtgacagtt gacagcgaca gctatcagtt gctcaaggca tatatgatgt    180
caatatctcc ggtctggtaa gcacaaccat gcagaatgaa gcccgtcgtc tgcgtgccga    240
acgctggaaa gcgaaaatc aggaagggat ggctgaggtc gcccggttta ttgaaatgaa    300
cggctctttt gctgacgaga acagggactg gtgaaatgca gtttaaggtt tacacctata    360
aaagagagag ccgttatcgt ctgtttgtgg atgtacagag tgatattatt gacacgcccg    420
ggcgacggat ggtgatcccc ctggccagtg cacgtctgct gtcagataaa gtctcccgtg    480
aactttaccc ggtggtgcat atcggggatg aaagctggcg catgatgacc accgatatgg    540
ccagtgtgcc ggtctccgtt atcggggaag aagtggctga tctcagccac cgcgaaaatg    600
acatcaaaaa cgccattaac ctgatgttct ggggaatata aatgtcaggc tccgttatac    660
acagccagtc tgcaggtcga cggtacccaa ggcggtggag aattcnnnnn nnnnnnnnnn    720
nnnnnnnnnn nnnnnnnnnn nnnnnnnnnn nnnngaatt caataaaaga tctttatttt    780
cattagatct gtgtgttggt tttttgtgtg tcgctacaat attttcctga acggaagaat    840
aaataaaact tgtcctgtaa agaaaaccca ggtaaaggaa agtggcagtc cagactgccc    900
ggaagttcct ggaggctaag gcctcacccc cgtcgcttga taggacctgc tgagccacat    960
gactaaggca cgatcgcctc cgcacgtgta aaggtgctgg gttccaagat ggctgccccg    1020
ccgcgaggcc cgacttaagt atgtcacttc cgcaccagcg agaaaggcgg acccttcagc    1080
caatgaggcc ataggggcggg gctaggccat gatgggcttt caaactaccc aatagggcgt    1140
ccgaactaaa gcgcctacaa agtaacgtca cgtcgagttg cagagcgccg gcaggcgggg    1200
cagaggtggc caagccaatg cgatggctgg ggcggggtcg acgctctat aagttgtcga    1260 taggcgggca ctccgcccta gattctaagg accgccgcca ccaccggtnn nnnnnnnnnn    1320
```

```
nnnnnnnnnn nnnnnnnnnn nnnnnnnnnn nnnnnnnntc tagataaatt cgtcagtagg   1380
gttgtaaagg ttttttttt cctgagaaaa caacctttg ttttctcagg ttttgctttt   1440
tggcctttcc ctagctttta aaaaaaaaaa gcaaaagacg ctggtggctg gcactcctgg   1500
tttccaggac ggggttcaag tccctgcggt gtctttgctt ggatccggct tactaaaagc   1560
cagataacag tatgcgtatt tgcgcgctga ttttgcggt ataagaatat atactgatat   1620
gtatacccga agtatgtcaa aaagaggtgt gctatgaagc agcgtattac agtgacagtt   1680
gacagcgaca gctatcagtt gctcaaggca tatatgatgt caatatctcc ggtctggtaa   1740
gcacaaccat gcagaatgaa gcccgtcgtc tgcgtgccga acgctggaaa gcggaaaatc   1800
aggaagggat ggctgaggtc gcccggttta ttgaaatgaa cggctctttt gctgacgaga   1860
acagggactg gtgaaatgca gtttaaggtt tacacctata aaagagagag ccgttatcgt   1920
ctgtttgtgg atgtacagag tgatattatt gacacgcccg ggcgacggat ggtgatcccc   1980
ctggccagtg cacgtctgct gtcagataaa gtctcccgtg aactttaccc ggtggtgcat   2040
atcggggatg aaagctggcg catgatgacc accgatatgg ccagtgtgcc ggtctccgtt   2100
atcggggaag aagtggctga tctcagccac cgcgaaaatg acatcaaaaa cgccattaac   2160
ctgatgttct ggggaatata aatgtcaggc tccgttatac acagccagtc tgcaggtcga   2220
cggatcc                                                             2227
```

DNA PLASMIDS FOR THE FAST GENERATION OF HOMOLOGOUS RECOMBINATION VECTORS FOR CELL LINE DEVELOPMENT

CROSS-REFERENCE TO RELATED APPLICATIONS

This application is a Continuation of U.S. patent application Ser. No. 16/346,614, filed May 1, 2019, which is a U.S. national stage application filed under 35 U.S.C. § 371 claiming benefit to International Patent Application No. PCT/US17/59816, filed Nov. 3, 2017, which is entitled to priority under 35 U.S.C. § 119(e) to U.S. Provisional Application No. 62/416,802, filed Nov. 3, 2016, each of which is hereby incorporated by reference in its entirety.

STATEMENT REGARDING FEDERALLY SPONSORED RESEARCH OR DEVELOPMENT

This invention was made with government support under R03DK105267 awarded by the National Institutes of Health (NIH). The government has certain rights in the invention.

BACKGROUND OF THE INVENTION

The recent discovery and development of enzymatic systems (TALENS, Zinc Finger Endonucleases, CRISPR) for targeting specific sequences of the DNA in living cells have dramatically enabled the modification of the genome of eukaryotic organisms. A common characteristic for these enzymatic systems is that once the target DNA sequence is recognized and cut, the endogenous DNA repair machinery will try to repair the double strand break by two main processes: The first process, known as Non-Homologus End Joining (NHEJ), will reconnect the two ends of the cut DNA in a multi-step process that is highly error proned, thus leaving small insertion or deletions of nucleotides in the repaired sequence. This natural mechanism has allowed the development of gene knockouts by promoting NHEJ in the sequence of the first exons of a target gene in order to alter the reading frame for protein translation with random mutations. The second process, known as Homology Directed Repair (HDR), requires a template of DNA with homology to both ends of the double strand break to repair the cut. This process is less error prone and has been widely used to repair or insert specific mutations of genetic diseases or to knock-in the sequence for protein markers such as purification tags or fluorescent proteins.

The donor templates that are used to promote HDR after a double strand break of the DNA, vary in size. They can be as simple as Single Strand DNA molecules (ssDNA) of less than 200 basepairs, or as large as donor plasmids containing homologous recombination arms for the 5' and 3' ends of the cut site. These donor vectors, also contain the sequence of the inserted protein markers and recombinant cassettes for the expression of a resistance gene to facilitate the isolation of modified cell clones. The construction of these donor plasmids is considered laborious and requires a multi-step process that can take a number of days to complete. Additionally, the selection of pure cell clones once the genomic modification is induced in the cells might require the use of expensive equipment for cell sorting, which is not available in every laboratory, or depend on cell selection with resistance cassettes against eukaryotic antibiotics, followed by single cell dilution, a process than can take multiple weeks to complete.

There is thus a need in the art for methods and compositions to accelerate the process of vector generation and pure clone cell selection. The present invention addresses this unmet need in the art.

SUMMARY OF THE INVENTION

In one embodiment, the invention relates to a homology directed recombination (HDR) donor vector comprising a nucleic acid molecule, wherein the nucleic acid molecule comprises one or more nucleotide sequences encoding a negative selection marker and a nucleotide sequence comprising an insertion cassette, wherein the insertion cassette comprises a nucleic acid sequence to be inserted into the genome of a cell.

In one embodiment, the insertion cassette comprises one or more of a cell selection marker sequence, a protein purification tag, a reporter marker sequence, a promoter sequence, a P2A linker sequence, a termination sequence, a mRNA stabilization sequence, a reporter marker sequence, a cell selection marker sequence, an exogenous gene or a combination thereof.

In one embodiment, the protein tag is one of chitin binding protein (CBP), maltose binding protein (MBP), glutathione-S-transferase (GST), poly(His), biotin/streptavidin, V5-tag, Myc-tag, HA-tag, NE-tag, His-tag, Flag tag, Halo-tag, Snap-tag, Fc-tag, Nus-tag, BCCP, Thioredoxin, SnooprTag, SpyTag, Isopeptag, SBP-tag, 5-tag, AviTag, Calmodulin.

In one embodiment, a reporter marker is one of chloramphenicol-acetyl transferase (CAT), β-galactosyltransferase, horseradish peroxidase, luciferase, NanoLuc®, alkaline phosphatase, and fluorescent proteins. In one embodiment, the fluorescent protein is selected from the group consisting of Green Fluorescent Protein (GFP), Red Fluorescent Protein (RFP), mCherry, mRuby3, mtagBFP2 and mClover3.

In one embodiment, the insertion cassette is one of a Zeocin™ resistance marker, a neomycin resistance marker, a puromycin resistance marker, a blasticidin resistance marker and a hygromycin resistance marker.

In one embodiment, the one or more negative selection markers comprises the ccdb gene. In one embodiment, the HDR donor vector comprises two nucleic acid sequences encoding negative selection markers flanking the insertion cassette. In one embodiment, the HDR donor vector of comprises a nucleic acid sequence as set forth in SEQ ID NO:1 or SEQ ID NO:2.

In one embodiment, the invention relates to an HDR vector comprising a nucleic acid molecule, wherein the nucleic acid molecule comprises one or more recombination arm, wherein the recombination arm comprises a nucleotide sequence having homology to a target nucleotide sequence, and a nucleotide sequence comprising an insertion cassette, wherein the insertion cassette comprises a nucleic acid sequence to be inserted into the genome of a cell.

In one embodiment, the insertion cassette comprises one or more sequences selected from the group consisting of a cell selection marker sequence, a protein purification tag, a reporter marker sequence, a promoter sequence, a termination sequence, a mRNA stabilization sequence, a reporter marker sequence, a cell selection marker sequence, an exogenous gene or a combination thereof.

In one embodiment, a protein tag is one of CBP, MBP, GST, poly(His), biotin/streptavidin, V5-tag, Myc-tag, HA-tag, NE-tag, His-tag, Flag tag, Halo-tag, Snap-tag, Fc-tag, Nus-tag, BCCP, Thioredoxin, SnooprTag, SpyTag, Isopeptag, SBP-tag, S-tag, AviTag, Calmodulin.

In one embodiment, a reporter marker is one of CAT, β-galactosyltransferase, horseradish peroxidase, luciferase, NanoLuc®, alkaline phosphatase, and fluorescent proteins. In one embodiment, the fluorescent protein is selected from the group consisting of GFP, RFP, mCherry, mRuby3, mtagBFP2 and mClover3.

In one embodiment, a cell selection marker sequence is one of a Zeocin™ resistance marker, a neomycin resistance marker, a puromycin resistance marker, a blasticidin resistance marker and a hygromycin resistance marker.

In one embodiment, the invention relates to a method of generating a genetically modified cell, comprising contacting a cell containing an endogenous chromosomal target DNA sequence with a HDR vector of the invention, such that homologous recombination between the one or more recombination arm of the HDR vector and the endogenous chromosomal target DNA sequence promotes integration of the insertion cassette of the HDR vector into the genome of the cell.

In one embodiment, the method of contacting comprises transfecting the cell with the HDR vector.

In one embodiment, the method further comprises providing a nuclease comprising an endonuclease domain that cuts DNA at a specific nucleotide sequence within the endogenous chromosomal target DNA in the cell; and contacting the endogenous chromosomal target DNA sequence with the nuclease, in the cell, such that the nuclease cuts or nicks the nucleotide sequence within the endogenous chromosomal target DNA sequence in the cell, thereby enhancing the frequency of homologous recombination between the endogenous chromosomal target DNA sequence and the one or more recombination arm of the HDR vector.

In one embodiment, the cell is from a human. In one embodiment, the cell is from a mouse.

In one embodiment, the invention relates to a genetically modified cell made according to the method of the invention. In one embodiment, a genetically modified cell is a knock-out cell. In one embodiment, a genetically modified cell is a knock-in cell. In one embodiment, the cell is a human cell. In one embodiment, the cell is a mouse cell.

In one embodiment, the invention relates to a method of generating a genetically modified animal in which a desired nucleic acid has been introduced, comprising: obtaining a primary cell comprising an endogenous chromosomal target DNA sequence into which it is desired to introduce said nucleic acid; contacting the cell with a HDR vector of the invention, such that homologous recombination between the one or more recombination arm of the HDR vector and the endogenous chromosomal target DNA sequence promotes integration of the insertion cassette of the HDR vector into the genome of the cell; and generating an animal from said primary cell in which homologous recombination has occurred.

In one embodiment, the method further comprises providing a nuclease comprising an endonuclease domain that cuts DNA at a specific nucleotide sequence within the endogenous chromosomal target DNA in the cell; and contacting the endogenous chromosomal target DNA sequence with the nuclease in the cell such that the nuclease cuts or nicks the nucleotide sequence within the endogenous chromosomal target DNA sequence in the primary cell, thereby enhancing the frequency of homologous recombination between the endogenous chromosomal target DNA sequence and the one or more recombination arm of the HDR vector.

In one embodiment, the animal is one of a mammal, a marsupial, an avian, an amphibian and a fish.

In one embodiment, the insertion cassette comprises a nucleotide sequence selected from the group consisting of a nucleotide sequence which disrupts a gene after homologous recombination, a nucleotide sequence which replaces a gene after homologous recombination, a nucleotide sequence which introduces a gene after homologous recombination, and a nucleotide sequence which introduces a regulatory site after homologous recombination.

In one embodiment, the invention relates to a genetically modified animal made according to the method of the invention.

In one embodiment, the invention relates to a method of treating a disease comprising introducing an HDR vector of the invention into a subject having a disease wherein the insertion cassette of the HDR vector comprises a nucleotide sequence selected from the group consisting of a nucleotide sequence which disrupts a gene after homologous recombination, a nucleotide sequence which replaces a gene after homologous recombination, a nucleotide sequence which introduces a gene after homologous recombination, and a nucleotide sequence which introduces a regulatory site after homologous recombination, wherein the gene is associated with the disease.

In one embodiment, the invention relates to a method of screening for the effect of a compound on one or more activity of a gene or protein comprising contacting one or more genetically modified cell of the invention, with the compound and evaluating one or more activity of a gene or protein. In one embodiment, the method comprises contacting a plurality of genetically modified cells of the invention with the compound.

In one embodiment, the invention relates to a method of treating a disease comprising administering to a subject in need thereof a compound identified by the method of screening for the effect of a compound of the invention as having an effect that is beneficial to the treatment of the disease. In one embodiment, the disease is associated with low levels of Heme oxygenase I (HO-1) expression, and the compound is one of disulfiram, thiostrepton, trimethadione, auranofin, thimerosal, halofantrine hycrochloride and vorinostat.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A depicts a HDR donor vector (or the backbone vector) is first digested with restriction enzymes to cut the segments with ccdB (controlling cell death B gene) cassettes (in this case KpnI and BamHI). FIG. 1B depicts synthetic recombination arms are designed having homology to a target DNA sequence. Recombination arms are mixed and cloned with the digested backbone vector by using the Gibson assembly method. FIG. 1C depicts the HDR vector product.

FIG. 2, comprising FIG. 2A depicts that a backbone vector is first digested with restriction enzymes to cut the segments with CDDB cassettes (in this case we use KpnI and BamHI). FIG. 2B depicts that previously designed synthetic recombination arms are mixed and cloned with the digested backbone vector by using the Gibson assembly method. FIG. 2C depicts the HDR vector product.

FIG. 3, comprising FIG. 3A depicts a HDR donor vector having a reporter sequence and an antibiotic resistance gene under control of an internal promoter is first digested with restriction enzymes to cut the segments with CDDB cassettes (in this case we use KpnI and BamHI). FIG. 3B depicts synthetic recombination arms are designed having homology to a target DNA sequence. Recombination arms are mixed and cloned with the digested backbone vector by using the Gibson assembly method. FIG. 3C depicts the HDR vector product.

FIG. 4, comprising FIG. 4A depicts exemplary constructs for inserting labeling tags in the C-terminal site of target genes. FIG. 4B depicts exemplary constructs for inserting labeling tags in the N-terminal site of target genes

FIG. 9, comprising FIG. 9A through FIG. 9C depicts representative images of a cell line developed with triple labeling. FIG. 9A depicts endogenous Histone 3, tagged with mRuby3. FIG. 9B depicts ATP5B, tagged with mTagBFP2. FIG. 9C depicts Beta Tubulin, tagged with mClover3. Cells were selected with a mix of Zeocin™, puromycin and blasticidin.

DETAILED DESCRIPTION

Figures 1A, 1B, 1C:
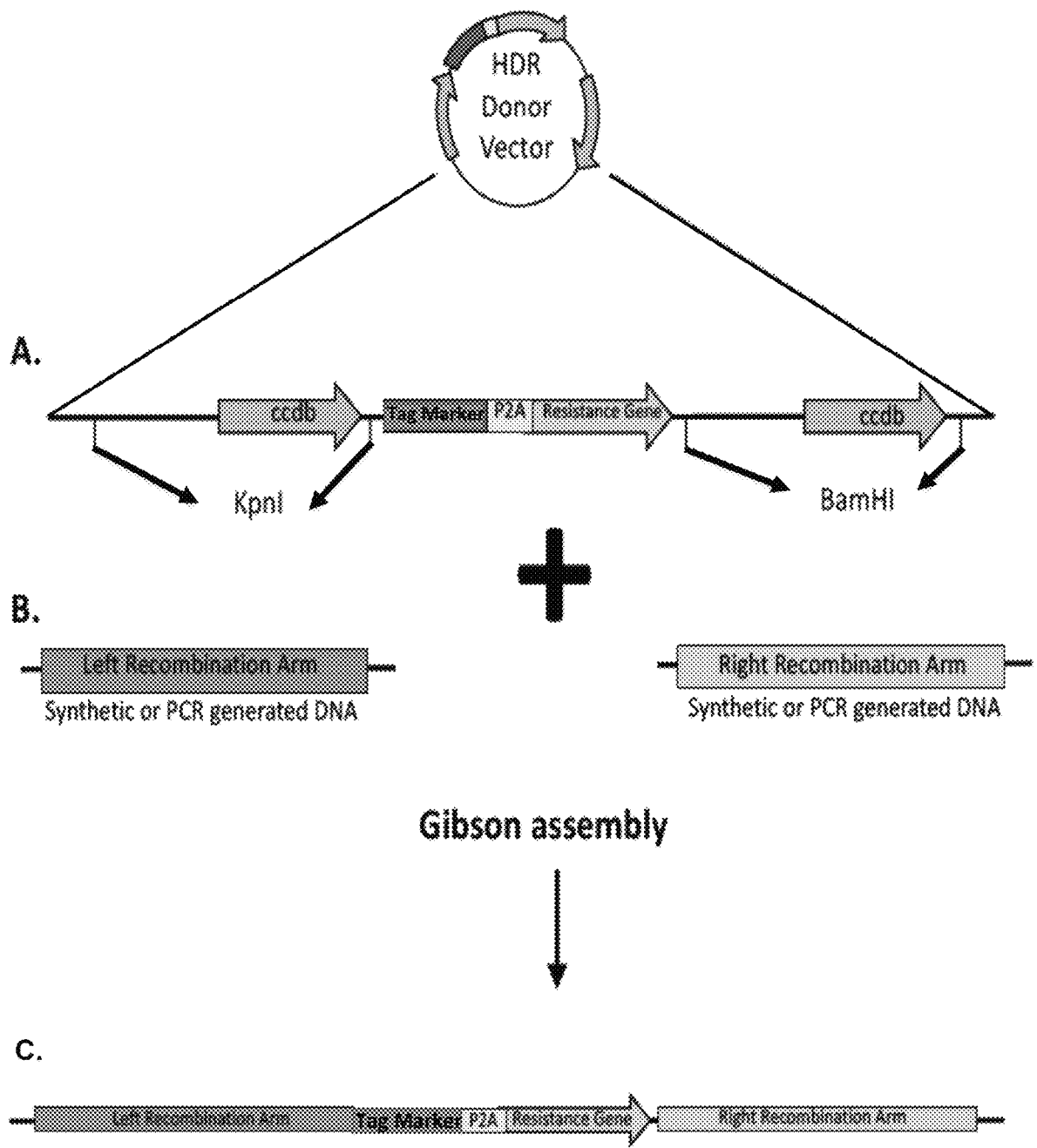
FIG. 1A through FIG. 1C, depicts a diagram of the components for constructing a HDR vector for C-terminal labeling.

In one embodiment, the invention provides methods and reagents for reducing the expression of one or more alleles of a gene. In one embodiment, the invention provides methods and reagents for labeling one or more alleles of a gene.

In one embodiment, the invention provides a DNA molecule for use in a method of targeting a region of a polynucleotide corresponding to an exogenous sequence. In one embodiment, the DNA molecule is a pre-recombination vector, or a HDR donor vector. In one embodiment, the DNA molecule is a recombination vector, or a HDR vector. In one embodiment, a HDR donor vector of the invention comprises an insertion cassette. In one embodiment, a HDR vector of the invention is generated through digestion of the HDR donor vector and ligation of the insertion cassette of the HDR donor vector to one or more nucleic acid sequences having homology to a target nucleic acid sequence.

In one embodiment, a HDR donor vector comprises one or more of a CCDB cassette and an insertion cassette. In one embodiment a HDR donor vector comprises a first CCDB cassette flanked by restriction enzyme cleavage sites for cleavage by a first restriction enzyme, an insertion cassette, and a second CCDB cassette flanked by restriction enzyme cleavage sites for cleavage by a second restriction enzyme. In one embodiment, a CCDB cassette comprises the ccdB gene encoding the CcdB toxin.

In one embodiment, an insertion cassette of a HDR donor vector comprises one or more of a polynucleotide sequence encoding a tag, a linker sequence, and an antibiotic resistance gene. In one embodiment, the linker sequence is a P2A sequence. In one embodiment, an exemplary nucleotide sequence of an HDR donor vector comprising a tag, a linker sequence, and an antibiotic resistance gene is set forth in SEQ ID NO:1.

In one embodiment, an insertion cassette comprises one or more of a polynucleotide sequence encoding a tag, a promoter sequence, and an antibiotic resistance gene. In one embodiment, the promoter is the EF-1 alpha promoter. In one embodiment, an exemplary nucleotide sequence of an HDR donor vector comprising a tag, a promoter sequence, and an antibiotic resistance gene is set forth in SEQ ID NO:2.

In one embodiment, a HDR vector is generated through ligation of the insertion cassette of the HDR donor vector to one or more nucleic acid sequences having homology to target nucleic acid sequence, or a recombination arm. In one embodiment, the HDR vector comprising two regions having homology to two target nucleic acid sequences, or two recombination arms. In one embodiment, the HDR vector comprises an insertion cassette flanked by two recombination arms.

In one embodiment, the HDR vector comprises a first region having a polynucleotide sequence corresponding to an exogenous sequence, an insertion cassette, and a second region having a polynucleotide sequence corresponding to an exogenous sequence. In one embodiment, the recombination vector (or a HDR vector) comprises a first region having a polynucleotide sequence corresponding to an exogenous sequence, a polynucleotide sequence encoding a tag, a linker sequence, a polynucleotide sequence encoding a protein for antibiotic resistance, and a second region having a polynucleotide sequence corresponding to an exogenous sequence. In some embodiments, the vector comprises a promoter. In one embodiment, the vector comprises a conditionally regulated promoter.

In one embodiment, the invention provides a method for tagging a gene or gene product in a cell, comprising: (a) introducing a HDR vector into a cell wherein the HDR vector comprises at least one polynucleotide sequence corresponding to an exon sequence of a gene, (b) selecting for a cell wherein the insertion cassette from the HDR vector has integrated into the genome.

In one embodiment, the invention provides a method for knocking down or knocking out a gene in a cell, comprising: (a) introducing a HDR vector into a cell wherein the HDR vector comprises at least one polynucleotide sequence corresponding to a promoter or exon sequences of a gene, (b) selecting for a cell wherein the insertion cassette from the HDR vector has integrated into the genome.

In one embodiment, the invention provides a method for tagging a plurality of genes or gene products in a cell, comprising: (a) introducing a plurality of HDR vectors into a cell wherein each HDR vectors comprises at least one polynucleotide sequence corresponding to an exon sequence of a gene and a unique insertion cassette, (b) selecting for a cell wherein a plurality of insertion cassette from the HDR vectors has integrated into the genome.

In another embodiment, the invention provides a method of producing a cell library, comprising: (a) introducing a plurality of HDR vectors into a plurality of cells wherein the HDR vectors each comprise a polynucleotide sequence corresponding to a promoter or exon sequence of a gene; (b) selecting for cells wherein the HDR vectors have integrated into the genome. In one embodiment, a cell library is a tagged cell library. In one embodiment, a library is a knockdown cell library. In one embodiment, a library is a knockout cell library.

In one embodiment, the invention includes a cell produced by a method of the invention. In one embodiment, the cell is a mammalian cell, and it may be a human cell. In certain embodiments, the invention includes cells comprising an integrated insertion cassette of the HDR vector of the invention. The invention also provides libraries, arrays, and collections of cells of the invention.

In another embodiment, the invention provides an animal produced by a method of the invention. In certain embodiments, the animal is a mammal, and in one embodiment, the animal is a mouse.

In one embodiment, a polynucleotide sequence of the HDR vector corresponds to a portion of a gene. In one embodiment, the gene is a reporter gene. In another embodiment, the gene is associated with a disease or disorder.

In certain embodiments of the invention, the integrated insertion cassette of the HDR vector is located in-frame 5' or 3' to a gene after recombination, serving to tag the targeted gene or protein. In certain embodiments of the invention, the integrated insertion cassette of the HDR vector is located in a transcribed region of a gene after recombination, serving to knockdown or knockout the targeted gene or protein.

In one embodiment, a cell of the invention comprises a disrupted gene. In some embodiments, the gene is disrupted by an integrated insertion cassette of an HDR vector. In certain embodiments, the insertion cassette further comprises a promoter, and in one embodiment, the promoter is an inducible promoter. In one embodiment, the insertion cassette is integrated into the genome of the cell.

In one embodiment, a cell comprises a single allele of a gene having an integrated insertion cassette after recombination. In an alternative embodiment, a cell comprises a both alleles of a gene having integrated insertion cassettes after recombination. The invention further provides a collection of cells of the invention, wherein each cell comprises a different disrupted gene.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

Allele: An "allele" is a single copy of a gene and may be one of a pair or of a series of copies or variant forms of a gene.

Allelic: The term "allelic" connotes the existence of more than one copy or form of a particular gene. Thus, a gene is said to be allelic if it has more than one allele.

As used herein, an "array" is an integral collection of objects that may be arranged in a systematic manner or in some predetermined fashion. An "array" can be, for example, an integral collection of vessels or an integral collection of wells. That is, an "array" can be a collection of objects that are formed as a unit with another part. An "array" also can be a surface upon which an integral collection of substances are arranged in a systematic manner.

An "array of cells" is a collection of cells, arranged in a systematic manner. An "array of cells," or a "cell array," represents, for example, a non-random arrangement of cell types or cells in which a gene is disrupted, contained within an integral collection of vessels or wells.

A "cell" of the instant invention may be, but is not limited to, a host cell, a target cell, a healthy cell, a mutated cell, a cell with disease or disorder characteristics ("diseased cell"), a transformed cell or a modified cell. A "cell" in this description may also denote a culture of such cells. A modified cell may be a cell that contains within its genome an integrated "construct" or an integrated "exogenous segment." Such a cell may be regarded as a "knockout." A modified cell may contain a polynucleotide whose expression is regulated by a biological factor or groups of such factors. In this respect, a modified cell may be a cell that contains a regulatable gene.

A "clone" is a number of cells with identical genomes, derived from a single ancestral cell. Thus, a group of genetically identical cells produced by mitotic divisions from one original cell, are "clones." According to the instant invention, a clone represents at least one cultured, preferably non-frozen cell, or plurality of such cells, each tracing its lineage to one cell.

The term "construct" denotes an artificially assembled polynucleotide molecule, such as a cloning vector or plasmid, that can exist in linear or circular forms. Typically, a construct will include elements such as a gene, a gene fragment, or a polynucleotide sequence of particular interest, juxtaposed with other elements in the construct, such as a cell selection marker, a reporter marker, an appropriate control sequence, a promoter, a termination sequence, a splice acceptor site, a splice donor site, and restriction endonuclease recognition sequences. A construct may be, for example, a "HDR donor vector" or a "HDR vector". A construct, or a part of it, may be integrated into a genome of a cell or into an in vitro-prepared preparation of a cell genome. "Disrupted" means the hindering of the expression of an endogenous gene product. In one embodiment, an allele of a gene is "disrupted" if any part of the allele nucleotide sequence contains a construct. Thus, a nucleotide sequence naturally present in a cell genome can be "disrupted" by the integration of another nucleotide sequence between a 5" end and a 3' end of the former sequence. The nucleotide sequence that disrupts a gene in a cell genome may be flanked by regions that, but for the presence of the sequence, together encode a polypeptide. Disruption of a gene by a construct, for example, may result in non-expression of a gene product in a cell or in the expression of a partially or totally non-functional gene product or an altered gene product.

A polynucleotide sequence in a construct is regarded as being downstream or 3' to a second polynucleotide sequence in the construct, if the 5' end of the former sequence is located after the 3' end of the latter sequence.

A nucleotide sequence is "exogenous" to a cell if it is not naturally a part of that cell genome, or it is deliberately inserted into the genome of the cell. A nucleotide sequence may be deliberately inserted into a cell genome by human intervention or automated means.

An exogenous nucleotide sequence, such as the sequence of a construct, or a portion thereof, may be referred to as an "exogenous segment." An exogenous segment may contain functional elements present in the intact construct, such as an antibiotic resistance gene.

A "gene" contains not only the exons and introns of the gene but also other non-coding and regulatory sequences, such as enhancers, promoters and the transcriptional termination sequence (e.g. the polyadenylation sequence). As used in this description, a gene does not include any construct that is inserted therein by human intervention or by automation. A gene may be allelic in nature.

The "genome" of a cell includes the total DNA content in the chromosomes of the cell, including the DNA content in other organelles of the cell, such as mitochondria or, for a plant cell, chloroplasts.

A "genomic sequence" of a cell refers to the nucleotide sequence of a genomic DNA fragment of the cell.

Suitable host cells may be non-mammalian eukaryotic cells, such as yeast, or preferably, prokaryotic cells, such as bacteria. For instance, the host cell may be a strain of $E.\ coli$.

The term "homologous recombination" refers to the process of DNA recombination based on sequence homology of nucleic acid sequences in a construct with those of a target sequence, such as a target allele, in a genome or DNA preparation. Accordingly, the nucleic acid sequences present in the construct are identical or highly homologous, that is, they are more than 60%, preferably more than 70%, highly preferably more than 80%, and most preferably more than 90% sequence identity to a target sequence located within a cell genome. In a particular embodiment, the homologous recombination vector has 95%-98% sequence identity to a target sequence located within a cell genome.

The word "integral" means formed as a unit with another part. Accordingly, applying the characterization of "integral" to a collection of elements, such as of wells or of vessels, indicates a purposeful accumulation of interrelated elements that are arranged in some predetermined fashion. An "integral" plurality of elements may refer to some but not necessarily to all elements of an array, for example. "Integral" also may be used to describe the contents within wells or vessels of an inventive array.

"Isolated" means to separate from another substance so as to obtain pure or in a free state. Accordingly, an "isolated polynucleotide," is a polynucleotide that has been separated from other nucleic acids, such as from a genome of a cell or from a genomic DNA preparation, or from other cellular compositions.

"Knockdown" means causing a reduction in the expression of one or more targeted genes or alleles. Knockdown may be accomplished by any of a variety of "knockdown reagents" or "knockdown molecules", and these terms are used interchangeably. "Knockdown reagents" include, for example, antisense RNA, ribozymes, and dsRNA. A "knockdown cell" refers to a cell comprising a knockdown reagent, and a "knockdown animal" refers to an animal comprising a knockdown reagent. Similarly, a "knockdown plant" refers to a plant comprising a knockdown reagent.

"Knockout" means having a specific single gene or allele(s) of a gene disrupted from a genome by genetic manipulation. Accordingly, a "single-allele, knockout cell" refers to a cell in which a single allele of a gene has been disrupted such that its gene product is not expressed. Similarly, a transgenic "knockout mouse" or other animal, is one that comprises cells containing a disrupted gene or allele.

In this description, "library" denotes an integral collection of two or more constituents. A constituent means "an essential part" of the library. A constituent of a library may be a cell or a nucleic acid. For instance, in addition to a cell library, a library may contain a collection of constructs, polynucleotides or RNA molecules. A library may contain a collection of selected drugs or compounds. A library may comprise an integral collection of "pooled" constituents physically present in one vessel. Alternatively, a library may be an integral collection of constituents produced by the inventive methodology that are stored separately from one another.

A "marker sequence" refers to either a cell selection marker sequence or a reporter marker sequence. A selection marker sequence encodes a selection marker and may be a host cell selection marker or a target cell selection marker. A reporter marker sequence encodes a reporter marker.

The term "naturally occurring" connotes to the fact that the object so qualified can be found in nature and has not been modified by human intervention. Thus, a nucleotide sequence is "naturally occurring" if it exists in nature and has not been modified by human intervention. If a polynucleotide is naturally occurring, the nucleotide sequence of the polynucleotide also is "naturally occurring." Likewise, if a genome of a cell is "naturally occurring," the nucleotide sequence of the genome is "naturally occurring."

A "nucleic acid" refers to DNA and RNA molecules. Thus, a vector, a plasmid, a construct, a polynucleotide, an mRNA or a cDNA are all examples of a nucleic acid.

A polynucleotide may be "obtained" by performing steps to physically separate the polynucleotide from other nucleic acids, such as from a cell genome. Alternatively, a polynucleotide may be "obtained" from a nucleic acid template by performing a PCR reaction to produce specific copies of the polynucleotide. Further still, a polynucleotide may be "obtained" by designing and chemically synthesizing the polynucleotide using nucleotide sequence information, such as that available in databases.

The term "operably linked" refers to a juxtaposition of genetic elements in a relationship permitting them to function in their intended manner. Such elements include, for instance promoters, regulatory sequences, polynucleotides of interest and termination sequences, which when "operably linked" function as intended. Elements that are "operably linked" are also "in frame" with one another.

Origin of replication: refers to a sequence of DNA at which replication is initiated.

Polynucleotide library: A polynucleotide library is an integral collection of at least two polynucleotides.

The term "random insertion" refers to the process by which a nucleic acid is integrated into an unspecified region of a genome or DNA preparation.

A "regulatable gene" is a gene or polynucleotide sequence whose transcription is modified or whose resultant mRNA transcript is degraded such that the transcript is not transcribed to produce a complete protein as encoded by the gene or polynucleotide sequence. A regulatable gene may be one whose mRNA, while intact, is not translated by the host cell enzymes. In general, a regulatable gene is one that permits its expression at specific times or under specific conditions. For instance, a regulatable gene is one which is driven by an inducible promoter.

An "insertion cassette" is a construct containing functional elements that facilitate the tagging, selection or both of a transformed cell in which the insertion construct has integrated. Such elements may include a "marker sequence" and "antibiotic resistance gene" nucleotide sequences. An "insertion cassette" may be designed to integrate into any part of a gene. In this regard, an "insertion cassette" may be a designed to integrate, in frame, downstream from a target gene. Alternatively, an "insertion cassette" may be a designed to integrate in the coding sequence of a gene, thereby disrupting the gene.

A polynucleotide sequence in a construct is regarded as being upstream or 5' to a second polynucleotide sequence in the construct, if the 3' end of the former sequence is located before the 5' end of the latter sequence.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to materials and methods by a gene can be tagged, modulated, mutated, "knocked-out" or otherwise disrupted, or "knocked-in" for exogenous gene expression in a cell. The present invention relates to HDR donor vectors which are modular backbones that can easily accommodate any tag and any selection antibiotic. The HDR donor vectors of the invention in combination with recombination arms are used to form HDR vectors which target and recombine the tag and selection marker into the genome of a target cell. Therefore, the present invention also relates to a method of using HDR vectors to produce a cell that contains one or more tagged or inactivated gene alleles. Cells generated using the methods of the invention are valuable in evaluating the therapeutic or diagnostic utilities of genes tagged, inactivated or expressed in these cells. Compositions In one embodiment, the invention relates to vectors for use in the method of the invention. In another embodiment, the invention relates to cells wherein one or more gene alleles has been tagged, inactivated or is expressed using the method of the invention.

HDR Donor Vector

An HDR donor vector of the invention provides a nucleic acid molecule comprising an insertion cassette. In one embodiment, an insertion cassette comprises a reporter marker, or a marker for recognition of a tagged gene. In one embodiment, an insertion cassette comprises a marker for purification of a tagged gene.

In one embodiment the insertion cassette is downstream from at least one negative selection marker cassette. In one embodiment the insertion cassette is upstream from at least one negative selection marker cassette. In one embodiment the insertion cassette is flanked by two negative selection marker cassettes. In one embodiment, the negative selection marker cassette comprises a toxin gene, or a nucleotide sequence for expression of a toxic product. In one embodiment, a toxin gene is ccdB. In one embodiment, a negative selection cassette containing the ccdB gene is a CCDB cassette. In one embodiment, the negative selection cassette is flanked by cleavage sites. In one embodiment, a cleavage site is a restriction enzyme cleavage site.

In one embodiment, the HDR donor vector of the current invention contains two negative selection cassettes to accelerate the cloning of the recombination arms to form the HDR vector. In one embodiment, an HDR donor vector comprises, in the 5' to 3' order, a first negative selection cassette, an insertion cassette, and a second negative selection cassette. In an exemplary embodiment, an HDR donor vector comprises, in the 5' to 3' order, a first CCDB cassette, an insertion cassette, and a second CCDB cassette. In one embodiment, each negative selection cassette is flanked by cleavage sites. In one embodiment, a cleavage site is a restriction enzyme cleavage site. In one embodiment, two negative selection cassettes are flanked by the same restriction enzyme cleavage site.

In an exemplary embodiment, an insertion cassette comprises, in the 5' to 3' order, a reporter marker and a cell selection marker. In one embodiment, the reporter marker and the cell selection marker are linked using a P2A fusion sequence.

In one embodiment, the HDR donor vector may include combinations of an origin of replication, cell selection marker sequences, mRNA stabilization sequence, exogenous gene sequence, termination sequence, internal ribosomal entry sequence (IRES), promoter sequences, translation initiation sequences, recombinase recognition sites, and other functional elements.

A reporter marker is a molecule, including polypeptide as well as polynucleotide, expression of which in a cell confers a detectable trait to the cell. In various embodiments, reporter markers include, but are not limited to, chloramphenicol-acetyl transferase (CAT), β-galactosyltransferase, horseradish peroxidase, luciferase, NanoLuc®, alkaline phosphatase, and fluorescent proteins including, but not limited to, green fluorescent proteins (e.g. GFP, TagGFP, T-Sapphire, Azami Green, Emerald, mWasabi, mClover3), red fluorescent proteins (e.g. mRFP1, JRed, HcRed1, AsRed2, AQ143, mCherry, mRuby3, mPlum), yellow fluorescent proteins (e.g. EYFP, mBanana, mCitrine, PhiYFP, TagYFP, Topaz, Venus), orange fluorescent proteins (e.g. DsRed, Tomato, Kusabria Orange, mOrange, mTangerine, TagRFP), cyan fluorescent proteins (e.g. CFP, mTFP1, Cerulean, CyPet, AmCyan1), blue fluorescent proteins (e.g. Azurite, mtagBFP2, EBFP, EBFP2, Y66H), near-infrared fluorescent proteins (e.g. iRFP670, iRFP682, iRFP702, iRFP713 and iRFP720), infrared fluorescent proteins (e.g. IFP1.4) and photoactivatable fluorescent proteins (e.g. Kaede, Eos, IrisFP, PS-CFP).

In one embodiment, the insertion cassette may include tags, e.g., to facilitate identification and/or purification of a target protein. Tags for use in the methods of the invention include, but are not limited to, chitin binding protein (CBP), maltose binding protein (MBP), glutathione-S-transferase (GST), poly(His), biotin/streptavidin, V5-tag, Myc-tag, HA-tag, NE-tag, His-tag, Flag tag, Halo-tag, Snap-tag, Fc-tag, Nus-tag, BCCP, Thioredoxin, SnooprTag, SpyTag, Isopeptag, SBP-tag, S-tag, AviTag, Calmodulin, or any combination of sequences appropriate for use in a method of tagging a protein. The target protein and associated tag can be purified from target cells or target cell culture medium by any method known in the art for purifying polypeptides. Examples of such methods include salt fractionation, high pressure liquid chromatography, antibody column chromatography, affinity tag column chromatography, and acrylamide gel electrophoresis. Such methods are well known to those skilled in the art.

A selection marker sequence can be used to eliminate target cells in which an insertion cassette has not been properly inserted or to eliminate host cells in which the HDR vector has not been properly transfected. A selection marker sequence can be a positive selection marker reporter marker or negative selection marker. Positive selection markers permit the selection for cells in which the gene product of the marker is expressed. This generally comprises contacting cells with an appropriate agent that, but for the expression of the positive selection marker, kills or otherwise selects against the cells. For suitable positive and negative selection markers, see Table I in U.S. Pat. No. 5,464,764.

Examples of selection markers also include, but are not limited to, proteins conferring resistance to compounds such as antibiotics, proteins conferring the ability to grow on selected substrates, proteins that produce detectable signals such as luminescence, catalytic RNAs and antisense RNAs. A wide variety of such markers are known and available, including, for example, a Zeocin™ resistance marker, a blasticidin resistance marker, a neomycin resistance (neo) marker (Southern & Berg, J. Mol. Appl. Genet. 1: 327-41 (1982)), a puromycin (puro) resistance marker; a hygromycin resistance (hyg) marker (Te Riele et al., Nature 348:649-651 (1990)), thymidine kinase (tk), hypoxanthine phosphoribosyltransferase (hprt), and the bacterial guanine/xanthine phosphoribosyltransferase (gpt), which permits growth on MAX (mycophenolic acid, adenine, and xanthine) medium. See Song et al., Proc. Nat'l Acad. Sci. U.S.A. 84:6820-6824 (1987). Other selection markers include histidinol-dehydrogenase, chloramphenicol-acetyl transferase (CAT), dihydrofolate reductase (DHFR), β-galactosyltransferase and fluorescent proteins such as GFP.

Expression of a fluorescent protein can be detected using a fluorescent activated cell sorter (FACS). Expression of β-galactosyltransferase also can be sorted by FACS, coupled with staining of living cells with a suitable substrate for β-galactosidase. A selection marker also may be a cell-substrate adhesion molecule, such as integrins which normally are not expressed by the mouse embryonic stem cells, miniature swine embryonic stem cells, and mouse, porcine and human hematopoietic stem cells. Target cell selection marker can be of mammalian origin and can be thymidine kinase, aminoglycoside phosphotransferase, asparagine synthetase, adenosine deaminase or metallothionien. The cell selection marker can also be neomycin phosphotransferase, hygromycin phosphotransferase or puromycin phosphotransferase, which confer resistance to G418, hygromycin and puromycin, respectively.

Suitable prokaryotic and/or bacterial selection markers include proteins providing resistance to antibiotics, such as kanamycin, tetracycline, and ampicillin. In one embodiment, a bacterial selection marker includes a protein capable of conferring selectable traits to both a prokaryotic host cell and a mammalian target cell.

Negative selection markers permit the selection against cells in which the gene product of the marker is expressed. In some embodiments, the presence of appropriate agents causes cells that express "negative selection markers" to be killed or otherwise selected against. Alternatively, the expression of negative selection markers alone kills or selects against the cells.

Such negative selection markers include a polypeptide or a polynucleotide that, upon expression in a cell, allows for negative selection of the cell. Illustrative of suitable negative selection markers are (i) herpes simplex virusthymidine kinase (HSV-TK) marker, for negative selection in the presence of any of the nucleoside analogs acyclovir, gancyclovir, and 5-fluoroiodoamino-Uracil (FIAU), (ii) various toxin proteins such as the diphtheria toxin, the tetanus toxin, the cholera toxin and the pertussis toxin, (iii) hypoxanthine-guanine phosphoribosyl transferase (HPRT), for negative selection in the presence of 6-thioguanine, (iv) activators of apoptosis, or programmed cell death, such as the bcl2-binding protein (BAX), (v) the cytidine deaminase (codA) gene of E. coli. and (vi) phosphotidyl choline phospholipase D. In one embodiment, the negative selection marker requires host genotype modification (e.g. ccdB, tolC, thyA, rpsl and thymidine kinases.)

In accordance with the present invention, the selection marker usually is selected based on the type of the cell undergoing selection. For instance, it can be eukaryotic (e.g., yeast), prokaryotic (e.g., bacterial) or viral. In such an embodiment, the selection marker sequence is operably linked to a promoter that is suited for that type of cell.

In another embodiment, more than one selection marker is used. In such an embodiment, selection markers can be introduced wherein at least one selection marker is suited for one or more of target or host cells. In one embodiment, the host cell selection marker sequence and the target cell selection marker sequence are within the same open-reading frame and are expressed as a single protein. For example, the host cell and target cell selection marker sequence may encode the same protein, such as blasticidin S deaminase, which confers resistance to Blasticidin for both prokaryotic and eukaryotic cells. The host cell and the target cell marker sequence also may be expressed as a fusion protein. In another embodiment, the host cell and the target cell selection marker sequence are expressed as separate proteins.

In one embodiment, expression of endogenous genes, selectable markers or reporters encoded by the insertion cassette of the invention may be driven from an endogenous promoter following integration of the cassette into the genome. Alternatively, or additionally, expression of markers or reporters may be driven from a promoter included within the insertion cassette of the HDR vector, which integrates into the genome together with the marker or reporter sequence. In certain embodiments, this promoter drives constitutive, high level expression of the marker or reporter gene, thereby facilitating selection or identification of cells having undergone a HDR event. One example of such a promoter is the EF-1 alpha promoter. In other embodiments, a promoter may be inducible and drive expression only when specific conditions are met.

A promoter can be selected based on the type of host or target cell or the desired level of expression of an exogenous gene. Suitable promoters include but are not limited to the ubiquitin promoters, the herpes simplex thymidine kinase promoters, human cytomegalovirus (CMV) promoters/enhancers, EF-1 alpha promoters, SV40 promoters, β-actin promoters, immunoglobulin promoters, regulatable promoters such as metallothionein promoters, adenovirus late promoters, and vaccinia virus 7.5K promoters. The promoter sequence also can be selected to provide tissue-specific transcription.

In certain embodiments, an IRES sequence may be included in the insertion cassette to improve the translation of a downstream gene. In one embodiment, the IRES may improve the translation of an exogenous gene sequences, a target cell selection marker sequence or a reporter marker sequence. The IRES site can be located within the insertion cassette and may be a mammalian internal ribosome entry site, such as an immunoglobulin heavy chain binding protein internal ribosome binding site. In one embodiment, the IRES sequence is selected from encephalomyocarditis virus, poliovirus, piconaviruses, picorna-related viruses, and hepatitis A and C. Examples of suitable IRES sequences can be found in U.S. Pat. No. 4,937,190, in European patent application 585983, and in PCT applications WO9611211, WO09601324, and WO09424301, respectively.

In one embodiment, a HDR donor vector comprises a translational initiation sequence or enhancer, such as the so-called "Kozak sequence" (Kozak, J. Cell Biol. 108: 229-41 (1989)) or "Shine-Delgarno" sequence. These sequences may be located in the insertion cassette, 3' to an IRES site but 5' to an endogenous gene sequence, reporter marker sequence or selection marker sequence.

In one embodiment, an insertion cassette of the invention comprises one or more mRNA stabilization sequence. An mRNA stabilization sequence may alter the half-life of an mRNA molecule encoding a target gene and fused to the sequence such that the reading frame is maintained. In one embodiment the mRNA stabilization sequence is a polynucleotide sequence that increases the half-life of a linked mRNA. In one embodiment the mRNA stabilization sequence is a polynucleotide sequence that decreases the half-life of a linked mRNA. In one embodiment, a mRNA stabilization sequence is a poly(A) tail which protects the mRNA molecule from enzymatic degradation in the cytoplasm. In one embodiment, a mRNA stabilization sequence is a MALAT1 3' stabilization sequence.

In one embodiment, a HDR donor vector comprises a transcription termination sequence. A typical transcriptional termination sequence includes a polyadenylation site (poly A site). In one embodiment, a poly A site is the SV40 poly A site. These sequences may be located in the insertion cassette, 3' to an endogenous gene sequence, reporter marker sequence or selection marker sequence.

In one embodiment, a HDR donor vector comprises one or more termination/stop codon(s) in one or more reading frames at the 3' end of an endogenous gene sequence, reporter marker sequence or selection marker sequence, such that translations of these sequences, if they encode polypeptides, are terminated at the stop codon(s).

Recombinase recognition sites may be used for insertion, inversion or replacement of DNA sequences, or for creating chromosomal rearrangements such as inversions, deletions and translocations. For example, two recombinase recognition sites in an insertion vector may be in the same orientation, to allow removal or replacement of the sequence between these two recombinase recognition sites upon contact with a recombinase. Two recombinase recognition sites may also be incorporated in opposite orientations, to allow the sequence between these two sites to be inverted upon contact with a recombinase. Such an inversion can be used to regulate the function of an insertion cassette or a portion thereof. Therefore, changing the orientation of the construct may switch on or off the construct's effect. For example, two recombinase recognition sites may flank a selection marker sequence, allowing removal or inactivation of the selection marker sequence. Examples of suitable recombinase recognition sites include frt sites and lox sites, which can be recognized by flp and cre recombinases, respectively.

In one embodiment, a HDR donor vector comprises an origin of replication capable of initiating DNA synthesis in a suitable host cell. Preferably, the origin of replication is selected based on the type of host cell. For instance, it can be eukaryotic (e.g., yeast) or prokaryotic (e.g., bacterial) or a suitable viral origin of replication may be used. Preferably, an origin of replication is capable of initiating DNA synthesis in the host cell but does not function in the target cell.

All of the above-described functional elements can be used in any combination to produce a suitable HDR donor vector.

HDR Vector

In one embodiment, a HDR vector of the invention comprises an insertion cassette flanked at either one end or both ends by endogenous nucleic acid sequence(s). The endogenous nucleic acid sequence(s) allow the HDR vector sequence to recombine with desired DNA sequences. The recombination event results in integration of the nucleic acid sequence of the insertion cassette into the target DNA. In one embodiment, the target DNA is genomic DNA of a target cell, therefore the insertion cassette is integrated into the genome of the target cell.

In one embodiment the nucleic acid sequence comprising the insertion cassette is downstream from at least one nucleotide sequence having homology to a genomic region of the target cell, or recombination arm. In one embodiment the insertion cassette is upstream from at least one recombination arm. In one embodiment the insertion cassette is flanked by two recombination arms.

In one exemplary embodiment, an HDR vector comprises, in the 5' to 3' order, a first recombination arm, an insertion cassette, and a second recombination arm, and the insertion cassette comprises a reporter marker sequence and a cell selection marker sequence. In one embodiment, the reporter marker sequence and the cell selection marker sequence are linked with a nucleic acid sequence encoding a P2A fusion sequence. Therefore, in one embodiment, the HDR vector comprises, in the 5' to 3' order, a first recombination arm, a reporter marker sequence, a P2A fusion sequence, a cell selection marker sequence, and a second recombination arm. Such an embodiment can be used, for example, for inserting a marker or tag, at the C-terminus of an endogenous gene.

In another exemplary embodiment, an HDR vector comprises, in the 5' to 3' order, a first recombination arm, an insertion cassette, and a second recombination arm, and the insertion cassette comprises a cell selection marker sequence and a reporter marker sequence. In one embodiment, the cell selection marker sequence and the reporter marker sequence are linked with a nucleic acid sequence encoding a P2A fusion sequence. Therefore, in one embodiment, the HDR vector comprises, in the 5' to 3' order, a first recombination arm, a cell selection marker sequence, a P2A fusion sequence, a reporter marker sequence, and a second recombination arm. Such an embodiment can be used, for example, for inserting a marker or tag at the N-terminus of an endogenous gene.

In yet another exemplary embodiment, an HDR vector comprises, in the 5' to 3' order, a first recombination arm, an insertion cassette, and a second recombination arm, and the insertion cassette comprises a reporter marker sequence, a promoter sequence and a cell selection marker sequence. In one embodiment, the reporter marker sequence and the cell selection marker sequence are linked with a nucleic acid sequence encoding a promoter sequence. Therefore, in one embodiment, the HDR vector comprises, in the 5' to 3' order, a first recombination arm, a reporter marker sequence, a promoter sequence, a cell selection marker sequence, and a second recombination arm.

In various embodiments, the insertion cassette of the HDR vector may include, but is not limited to, any combination of exogenous gene sequence, reporter marker sequence, cell selection marker sequence, mRNA stabilization sequence, termination sequence, IRES, promoter sequence, translation initiation sequence, recombinase recognition sites, and other functional elements, as described in detail above.

In various embodiments, a recombination arm may be at least about 25 bp, at least 25-50 bp, at least 50-100 bp, at least 100-300 bp, at least 300-1000 bp, at least 1000-2000 bp, at least 2000-5000 bp, at least 5000-7000 bp or more than 7000 bp. In various embodiments a recombination arm comprises a nucleic acid sequence having more than 60%, more than 70%, more than 80%, more than 90%, more than 95%, more than 98%, or 100% sequence identity to a target nucleic acid sequence. In one embodiment, a target nucleic acid sequence is a genomic DNA sequence. The instant invention is not limited as to the genomic location which a recombination arm targets. That is, a recombination arm may have more than 60%, more than 70%, more than 80%, more than 90%, more than 95%, more than 98%, or 100% sequence identity to an exonic sequence, an intronic sequence, an intergenic sequence, a 3' UTR sequence, a 5' UTR sequence, a promoter sequence, a chromosomal sequence or an extrachromosomal sequence.

In one embodiment, a HDR vector has two recombination arms flanking an insertion cassette. In one embodiment, the two recombination arms may target sequences proximal to each other. The genomic sequence targeted by the two recombination arms may be non-continuous or continuous in the genome of the target cell before integration of the insertion cassette. As used herein, two nucleotide sequences are continuous if the 3' end of one nucleotide sequence is covalently linked to the 5' end of the other nucleotide sequence without any intervening nucleotide residue. In one embodiment, two recombination arms target genomic sequences less than 10 kb, less than 9 kb, less than 8 kb, less than 7 kb, less than 6 kb, less than 5 kb, less than 4 kb, less than 3 kb, less than 2 kb or less than 1 kb apart. In one embodiment, two recombination arms target genomic sequences more than 10 kb, more than 9 kb, more than 8 kb, more than 7 kb, more than 6 kb, more than 5 kb, more than 4 kb, more than 3 kb, more than 2 kb or more than 1 kb apart.

The HDR vector can be prepared in various ways. For example, the first and second recombination arm may be obtained from available genome database or gene expression database for human or other species. The two sequences may be amplified with primers designed to incorporate restriction enzyme cleavage sites, digested with restriction enzymes and then ligated into a digested HDR donor vector using methods as appreciated in the art. In one embodiment, two recombination arms are ligated with a digested HDR donor vector to generate a HDR vector using the Gibson assembly method (Gibson et al., Nat Methods, 2009, 6:343-345). In one embodiment, a HDR vector generated using the Gibson assembly method is linear, such that the linearized product comprises: (1) a first recombination arm (2) an insertion cassette, having a reporter marker, a selection marker or a combination thereof; and (3) a second recombination arm. This linearized product is a preferred HDR vector of the present invention.

Cells

A HDR vector of the present invention can be used to tag, knock-in or knock-out genes in the genome of any type of target cell. A HDR vector can be introduced into a target cell by any methods as appreciated in the art, including but not limited to, electroporation, viral infection, retrotransposition, microinjection, lipofection, liposome-mediated transfection, calcium phosphate precipitation, DEAE-dextran, and ballistic or "gene gun" penetration.

Special chemicals or constructs may be provided to increase recombination levels and therefore promote integration of the insertion cassette. In one embodiment, such a construct may provide a nick (cleavage of one strand of a double-stranded DNA molecule) or cut (cleavage of both strands of a double-stranded DNA molecule) at or near the target sequence of one or more recombination arm of the HDR vector. Therefore, in one embodiment, the HDR vector of the invention may be provided in combination with one or more constructs encoding TALENS, Zinc Finger Endonucleases, CRISPR or another method of generating a nick or cut near the target sequence of one or more recombination arm of the HDR vector.

In one embodiment, target cells are prokaryotic cells. In one embodiment, target cells are eukaryotic cells. In one embodiment, a target cell is a mammalian cell, such as a murine or human cell. The target cell may be a somatic cell or a germ cell. The germ cell may be a stem cell, such as embryonic stem cells (ES cells), including murine embryonic stem cells. The target cell may be a non-dividing cell, such as a neuron, or alternatively, the target cell can proliferate in vitro under certain culturing conditions.

The target cell may be chosen from commercially available mammalian cell lines. The target cell may be a primary cell isolated from a subject. A target cell may be any type of diseased cell, including cells with abnormal phenotypes that can be identified using biological or biochemical assays. For instance, the diseased cell may be a tumor cell.

In one embodiment, a reporter sequence in the insertion sequence of an HDR vector integrates in-frame downstream from at least one allele of at least one gene in a target cell's genomic DNA, serving to tag the gene. Cells that have a single gene tagged by insertion of a construct have become singly tagged. Cells that have multiple genes tagged by insertion of a multiple constructs have become multiply tagged. In one embodiment, the invention relates to libraries of singly or multiply tagged cells.

Libraries

Based upon the information provided herein, numerous polynucleotide and cell libraries can be produced. These libraries include, but are not limited to, libraries of (i) HDR donor vectors, (ii) HDR vectors, (iii) cells with a single tagged gene, (iv) single gene knock-out cells, produced by integration of an insertion cassette into a gene, (v) single gene knock-in cells, produced by integration of an insertion cassette for expression of an exogenous gene into the genome of a cell, (vi) cells with multiple tagged genes, (vii) multi-gene knock-out cells, produced by integration of multiple insertion cassettes into multiple genes and (viii) multi-gene knock-in cells, produced by integration of an insertion cassette for expression of multiple exogenous genes into the genome of a cell.

In one embodiment, a HDR vector library may be constructed using information within a genome database or a gene expression database. For example, each gene in the genome database or the gene expression database may be identified and a HDR vector directed to the gene may then be prepared. In one embodiment, a HDR vector library may comprise vectors for tagging genes. In one embodiment, a HDR vector library may comprise vectors for generation of knock-in cells. In one embodiment, a HDR vector library may comprise vectors for generation of knock-out cells. The HDR vectors so prepared compose a vector library, representing the entire set of the genes, or any subset thereof, in the genome database or the gene expression database. A target cell selection marker sequence, a reporter marker sequence, or a combination thereof may be included in each HDR vector.

A cell library of the present invention may comprise, for example, at least 2 or more cells. A cell library may contain between 5-10 cells, 10-20 cells, 20-30 cells, 30-40 cells, 40-50 cells, 50-100 cells, 100-500 cells, 500-1,000 cells, 1,000-5,000 cells, 5,000-10,000 cells, 10,000-20,000 cells, 20,000-50,000 cells or more than 50,000 cells.

The cell library may represent, for example, anywhere from 1 to 25 tagged, expressed, modified or disrupted genes, at least about 25 different genes, or at least about 50 different genes, preferably at least about 100 different genes, more preferably 1,000 different genes, highly preferably 5,000 different genes, and most preferably 10,000 different genes, such as at least 20,000 different genes. For example, the cell library may represent at least about 40,000, or at least about 75,000, different genes. Each of these represented genes corresponds to a cell in the cell library, and at least one allele of the gene is tagged, expressed, modified or disrupted in the corresponding cell by an insertion cassette, preferentially, more than one allele of the gene is tagged, expressed, modified or disrupted. In one embodiment, the cell library consists of clones of a single parent cell. The number of tagged, expressed, modified or disrupted genes in the cell library may be up to the maximum number of genes present in the genome of the parent cell.

A cell library can be essentially a collection of cells, either maintained in individual liquid stocks or grown as a mixed, single liquid stock. A cell library, therefore, may be a collection of cell cultures each of which represents cells containing an allele tagged, modified or disrupted by the inventive methodology. In this regard, a cell library containing alleles tagged, modified or disrupted by a construct of the instant invention, also may comprise cell colonies isolated on growth media in a culture dish. For instance, each colony on the culture dish can comprise a tagged, expressed, modified or disrupted gene that may be the same gene tagged, expressed, modified or disrupted in other colonies that are stored on the same culture dish.

In one embodiment, the cell library may comprise a mixture of cell cultures in one liquid stock solution. A cell culture may contain the same or different tagged, expressed, modified or disrupted gene to another cell culture in the library. In one embodiment, therefore, the tagged, expressed, modified or disrupted gene in a given cell in a cell library is different from the tagged, expressed, modified or disrupted gene in any other cell of the library. The cell library of this embodiment may be part of or a subset of another cell library.

In one embodiment, a cell library may contain cells each of which contain the same tagged, modified or disrupted gene. In this case, the function of the insertion cassette (e.g. expression of a full length protein vs expression of a protein fragment) may be the same or different for each cell.

In one embodiment, a cell library of the present invention may be prepared by introducing a library of HDR vectors into a plurality of target cells. These HDR vectors, comprising a target cell selection marker sequence, may insert into the genomes of the target cells, tagging, expressing or disrupting different genes in the genomes. The modified cells may be selected for the selectable trait conferred by the target cell selection marker sequence.

In one embodiment, mouse ES cells, such as early passage mouse ES cells, are used to construct a cell library of the present invention. The cell library thus made becomes a genetic tool for the comprehensive study of the mouse genome. Since ES cells can be injected back into a blastocyst and incorporated into normal development and ultimately the germ line, the mutated ES cells in the library effectively represent collection of mutant transgenic mouse strains. The resulting phenotypes of the mutant transgenic mouse strains, and therefore, the function of the disrupted genes, may be rapidly identified and characterized. The resulting transgenic mice may also be bred with other mouse strains and back crossed to produce congenic or recombinant congenic animals that allow for the evaluation of the targeted gene in different genetic backgrounds. A representative listing various strains and genetic manipulations that can be used to practice the above aspects of the present invention (including the ES cell libraries) can be found in Genetic Variants and Strains of the Laboratory Mouse, 3rd Ed., Vols. 1 and 2, Oxford University Press, New York, 1996.

A similar methodology can be used to construct virtually any non-human transgenic or knockout animal. These non-human transgenic or knockout animals include pigs, rats, rabbits, cattle, goats, non-human primates such as chimpanzee, and other animal species, particularly mammalian species.

Any HDR vector described in the present invention can be employed to make a cell, a cell library, or a transgenic or knockout animal, as described above.

Methods

The instant invention provides a method for tagging a protein or generating a fusion protein in a cell. Generally, the method comprises the steps of (a) inserting a HDR vector of the present invention into a cell, wherein the HDR vector comprises an insertion cassette comprising a reporter marker, a target cell selection marker sequence, or both; and (B) placing the cell under conditions for selection of a cell selection marker encoded by the insertion cassette of the HDR vector or monitoring the expression of a reporter marker sequence.

In one embodiment, the recombination arms of the HDR vector hybridize to the homologous genomic region, and recombination between the recombination arms of the HDR vector and the genome allows integration of the insertion cassette of the HDR vector into the genome of the target cell. In one preferred embodiment, the insertion cassette comprising a reporter marker, a target cell selection marker sequence, or both integrates downstream of an open reading frame in a manner such that the reading frame is not disrupted (i.e. in-frame integration), allowing for generation of a tagged or fusion protein.

In one embodiment, the method further comprises inserting a DNA nuclease into the target cell. In one embodiment, the nuclease is specific for generating a nick or cut at or near the homologous genomic sequence of one or more of the recombination arms of the HDR vector. The nuclease may be, but is not limited to, a meganuclease, a Cas-9 nuclease, a TALEN, a ZFN, or another nuclease useful for a method of genome editing.

In one embodiment, one allele of a gene is modified through the method of the invention. In another embodiment, all the alleles of the same gene in a cell are modified through the method of the invention.

The invention provides methods of reducing the expression of an endogenous gene in a cell, plant or animal by introducing an insertion cassette into the endogenous gene such that expression of the gene is disrupted. Thus, the invention provides an efficient and precise way to produce a "knockout" cell that is unable to produce a transcript or to express a gene product. The target cells thus made, are useful to evaluate the therapeutic or diagnostic utilities of the inactivated genes, and to screen for compounds that affect the expression and function of the genes.

In one embodiment, method of the invention may be used to indirectly modulate the expression of a gene whose expression is regulated (e.g. activated or inhibited) by a target gene. The effect of the targeted gene upon the regulated gene may be normal, or it may be a consequence of an abnormal imbalance induced by a disease state.

The invention also provides methods of expressing of an exogenous gene or polynucleotide sequence (e.g. transgene) in a cell, plant, or animal. Thus, in one embodiment, the invention provides a knock-in method for expressing a gene in a cell. The exogenous sequence may be on an insertion cassette and integrated into the genome of the cell, plant, or animal. In one embodiment, the integration site for the insertion cassette comprising an exogenous gene is intergenic. Transcription of the exogenous gene in the cell may be regulated by either an exogenous promoter or an endogenous promoter. Accordingly, in one embodiment, the insertion cassette comprising the exogenous gene further comprises a promoter sequence. In certain embodiments, the promoter driving expression of the exogenous gene is conditionally regulated, by any available method, including those described above. In some embodiments of the invention, an exogenous gene may be operably linked to a tag, a reporter marker, a selection marker, or any combination of functional elements as described previously.

A variety of exogenous genes may be introduced into a cell, plant or animal and regulated according to a method of the invention. For example, a gene associated with a disease or disorder may be introduced into a cell. In certain situations, the invention provides a method of replacing an absent, mutated or otherwise dysfunctional gene. In other embodiments, a therapeutic polynucleotide may be introduced into a cell. In addition to providing a missing gene or protein, the therapeutic molecule may act by any of a variety of other means, including, for example, to inhibit the function of another molecule, e.g. a dominant-negative.

Method of Using the Cells

HDR vectors may be prepared and used to activate, inactivate or tag any one or a combination of genes in cells. In one embodiment, the gene or combination of genes are associated with a disease phenotype. In one embodiment, the gene or combination of genes are not associated with a known diseased phenotype. The cells thus modified may be screened for a diseased phenotype in order to identify the gene or genes that may be involved in the development of the phenotype. A HDR vector with a reporter marker also may be used to tag a gene or combination of genes that is associated with a disease phenotype.

When a HDR vector comprises a target cell selection marker sequence or a reporter marker sequence and is inserted into a gene in the genome of a target cell, such that the selection or reporter marker sequence are expressed under a variety of circumstances, then the target cell can be used for drug discovery and functional genomics. The target cell that reports the modulation of the expression of the selection marker or the reporter marker sequence in response to a variety of stimuli, such as hormones and other physiological signals, may be identified. Thus, the gene disrupted in the target cell is involved in responding to the stimuli. These stimuli may relate to a variety of known or unknown pathways that are modulated by known or unknown modulators. Chemicals that modulate the target cell's response to the stimuli also can be identified.

In one embodiment, modified cells of the invention can be used to screen for drugs or compounds that regulate (e.g. reduce or increase) the expression of the targeted genes. In one embodiment, the HDR vector also comprises a reporter marker sequence. A drug or compound library may be applied to the target cell, in which the reporter marker sequence is inserted into an expressed gene, to screen for candidates that may regulate the expression of the reporter marker sequence, and therefore, the expression of the gene.

In one embodiment, the cell in which one, two or multiple genes are disrupted or tagged by an insertion cassette from an HDR vector, may be used to screen for compounds that regulate the expression of one tagged gene but do not regulate expression of another. For example, to identify compounds that regulate the expression of a tagged gene associated with a disease phenotype but not a housekeeping gene or a closely related gene. Therefore, in one embodiment, the present invention can be used to determine the specificity of drug candidates on a chosen target gene.

In one embodiment, modified cells of the invention can be used to identify compounds capable of inducing expression of a silent gene in a target cell. For instance, an insertion cassette from an HDR vector may integrate in a target cell may be incorporated into the genome of the target cell. In such an embodiment, a selection marker encoded by the integration cassette may be operably linked to a promoter sequence and therefore expressed independently of a reporter marker that serves to tag a target gene. Compounds or drugs that are capable of inducing transcription of the non-actively transcribed genomic sequence can therefore be identified by screening for the reporter marker.

Formulation and Administration

An HDR vector molecule of the present invention may be administered to a subject. In accordance with the invention, therefore, the HDR vector may be prepared in a suitable formulation for in vivo administration. The subject may be any animal, such as a mouse or a rat, or the subject may be a human. An HDR vector may function in vivo as a drug, in the sense that, in some embodiments, insertion of the integration cassette may (1) induce expression of a gene that is not expressed normally or (2) reduce expression of a gene that is over-expressed due to some genetic disorder or abnormality. In this regard, administering an amount of a HDR vector of the instant invention that is effective in modulating the expression pattern of a specific gene represents a therapeutic application.

More than one HDR vector molecule may be administered simultaneously or sequentially, to a subject or to cells in vitro. For example, HDR vectors designed to different sequences or regions of a gene can be pooled and administered as one formulation.

To facilitate the use of an inventive HDR vector as a therapeutic agent, the molecule, for example, a linear dsDNA, may be protected against nucleic acid degradation by any one of a number of known techniques, for instance, encapsulated within a liposome prior to administration. A formulation of nucleic acid and polyethylene glycol, for instance, may also increase the half-life of the nucleic acid in vivo, as could any known slow-release nucleic acid formulation. Other methods may be used to protect and enhance the bioavailability of a nucleic acid. For example, a thiol group may be incorporated into a polynucleotide, such as into an RNA or DNA molecule, by replacing the phosphorous group of the nucleotide. When so incorporated into the "backbone" of a nucleic acid, a thiol can prevent cleavage of the DNA at that site and, thus, improve the stability of the nucleic acid molecule. Other modifications include, for example, a nucleic acid molecule backbone may be modified so as to contain phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included. Yet another method of modifying a nucleic acid of the instant invention involves the production of a "locked nucleic acid" (LNA).

Use of Compounds

In one embodiment, compounds or molecules identified in a screen using genetically modified cells are useful for treatment of a disease associated with an activity of a gene targeted by the HDR vector of the invention. Therefore, the invention relates to a method of treating a disease comprising administering to a subject in need thereof a compound identified by the method of screening for the effect of a compound of the invention. In one embodiment, the compound was identified in the screen as having an effect on one or more of the expression or activity of a targeted gene. In one embodiment, the effect in an increase in the expression or activity of the targeted gene. In one embodiment, the effect is a decrease in the expression or activity of the targeted gene. In one embodiment, increasing or decreasing the expression or activity of a gene is beneficial to the treatment of the disease.

In one embodiment, the disease is associated with low levels of Heme oxygenase I (HO-1) expression. In one embodiment, disulfiram, thiostrepton, trimethadione, auranofin, thimerosal, halofantrine hycrochloride and vorinostat were identified in a screen of cells tagged with an HDR vector of the invention as increasing the expression level of HO-1. Therefore, in one embodiment, one of disulfiram, thiostrepton, trimethadione, auranofin, thimerosal, halofantrine hycrochloride and vorinostat may be administered to a subject for whom an increased level of HO-1 expression would be beneficial for the treatment of a disease.

Pharmaceutical Compositions

The present invention includes pharmaceutical compositions comprising one or more modulators of a gene targeted by an HDR vector of the invention. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, intratumoral, epidural, intracerebral, intracerebroventricular, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: An Efficient Method for the Fast Generation of Homologous Recombination Vectors for Cell Line Development A novel set of plasmids and a streamlined methodology that allows the construction of donor vectors for HDR repair in a single step has been developed. The novel vectors allow the insertion of multiple tags for downstream applications such as fluorescent labeling (mClover3 and mRuby3), luminescence (NanoLuc®) and protein purification tags (3×-flag, Halo-tag). Also, these vectors allow in-frame expression of eukaryotic antibiotics (Puromycin, Zeocin™, Blasticidin, etc) for rapid selection of modified cells.

A backbone plasmid was developed to facilitate the creation of Homologous Recombination vectors for gene knockin or knockout generation of cell lines and organisms.

Figures 2A, 2B, 2C:
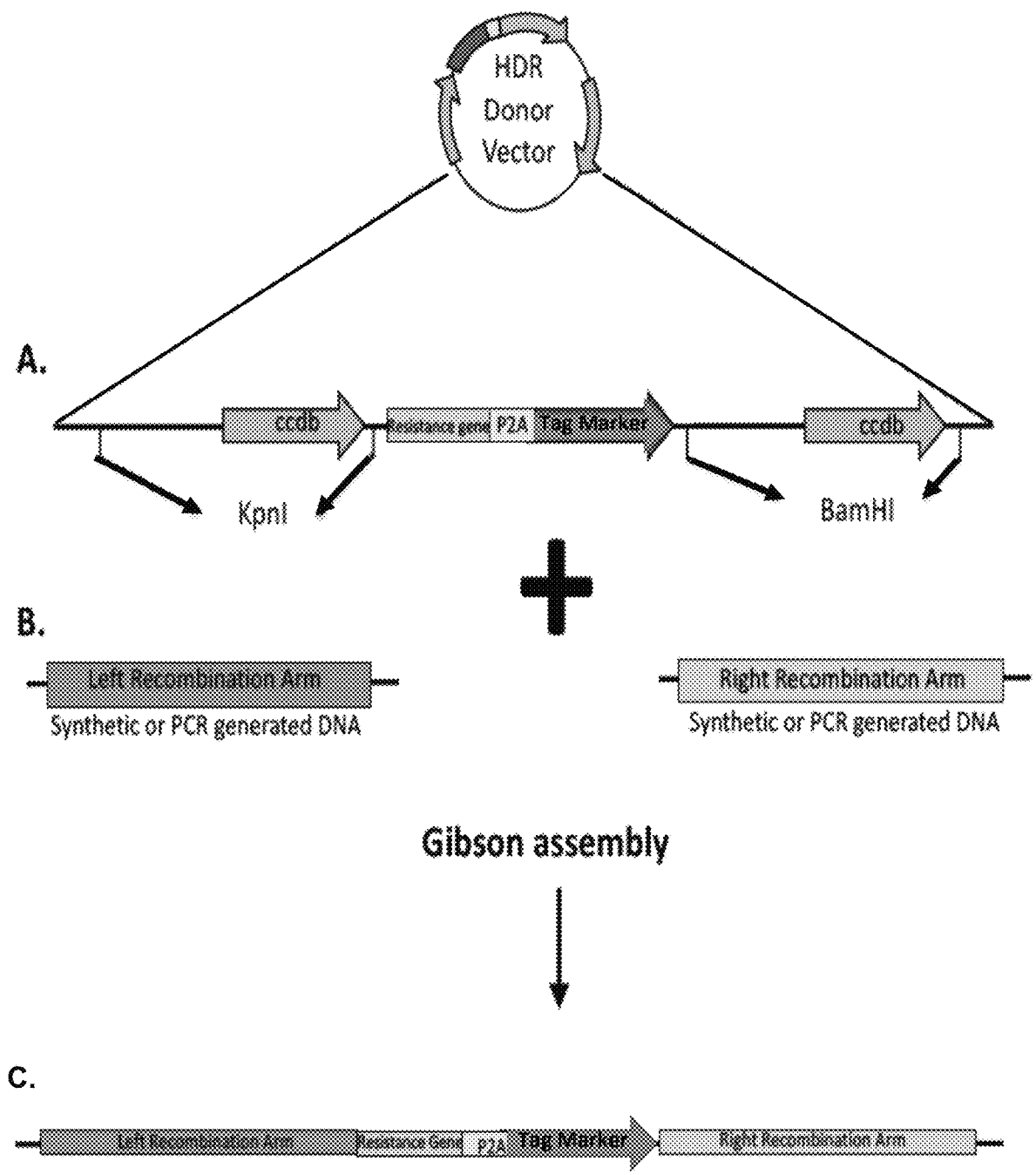
FIG. 2A through FIG. 2C, depicts a diagram of the components that are required for constructing a HDR vector for N-terminal labeling.
Figures 3A, 3B, 3C:
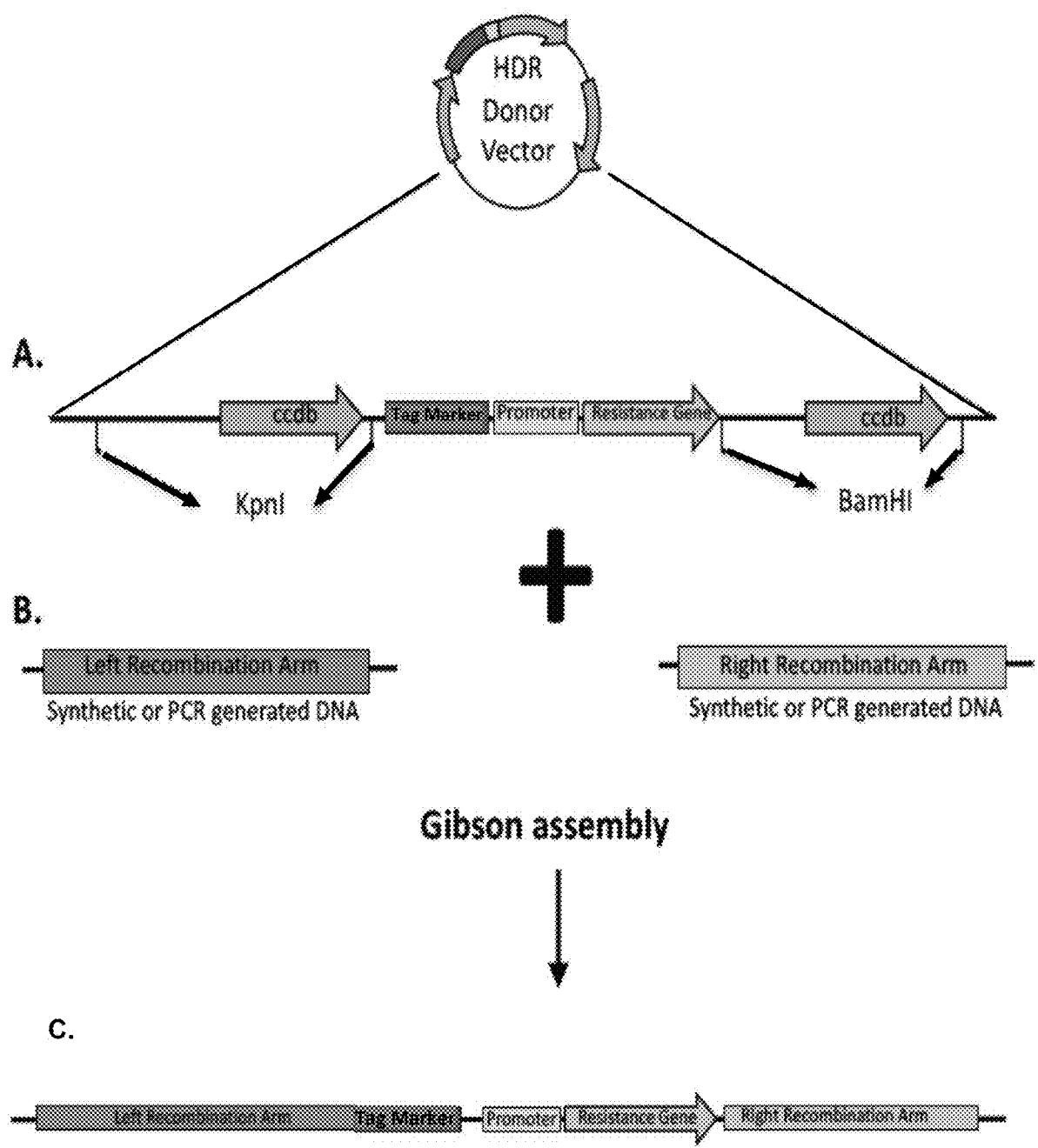
FIG. 3A through FIG. 3C, depicts a diagram of the components that are required for constructing a HDR vector with an internal promoter.

The system contains multiple characteristics to accelerate the process of vector generation and pure clone cell selection. This includes cloning of the left and right recombination arms in a single step with 100% accuracy. This is possible due to the incorporation of dual expression cassettes for the toxic protein CcdB. The two CcdB cassettes must be replaced with the recombination arms in order to obtain viable E. coli colonies (FIG. 1 through FIG. 3).

Figure 4A:
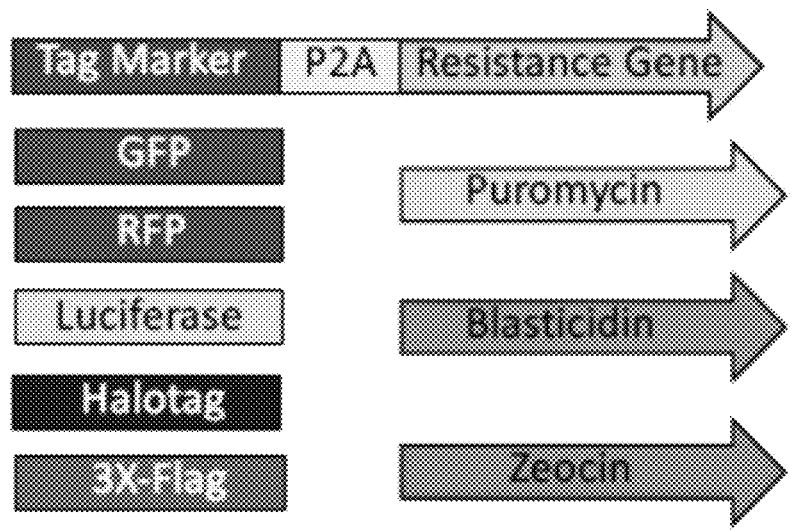
FIG. 4A through FIG. 4B, depicts a diagram of examples of protein tags that can be used to label endogenous proteins by facilitating homologous recombination.
Figure 4B:
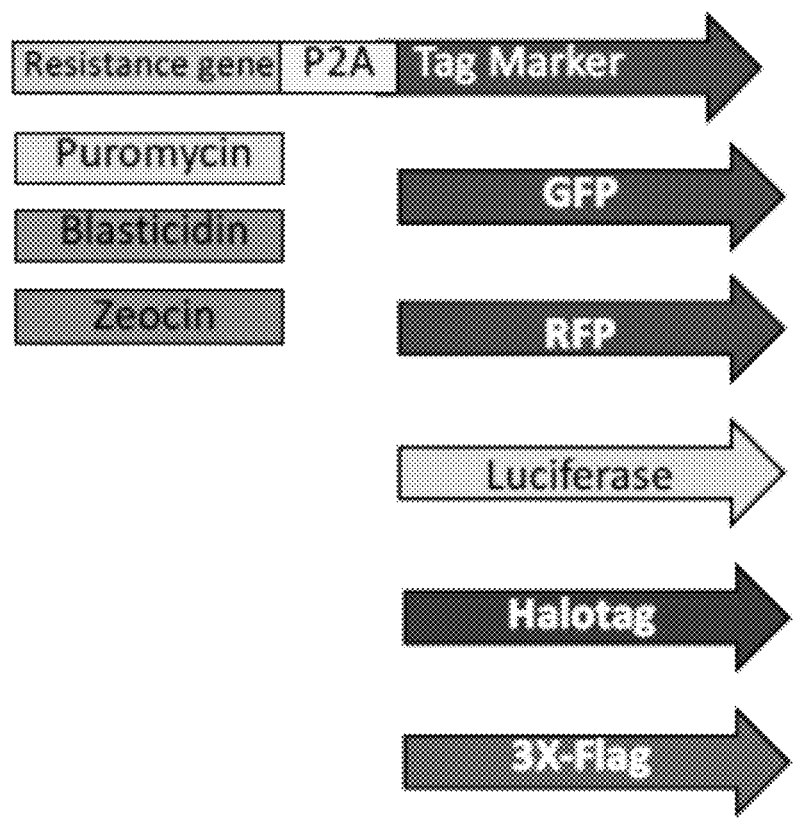

The backbone can be quickly modified to include any protein marker for protein tagging. As an example, vectors with fluorescent proteins (mClover3, mRuby3), luminicense (NanoLuc®) and purification tags (Halotag and 3×-Flag) have all been generated (FIG. 4).

The backbone can be quickly modified to include any resistance gene against toxic antibiotics for eukaryotic cells. As an example, vectors with resistance genes against Puromycin, Blasticidin and Zeocin have all been created (FIG. 4).

The system allows the selection of pure clones of modified cells in less than 10 days by allowing the expression of the resistance gene only in the cells that were modified by homologous recombination.

The system allows the user to test multiple tags (Fluorescence, Luminescence, tag for protein purification, etc) against the same target gene by designing only 1 set of homologous recombination arms and cloning those in different vectors with each of the tags of interest.

The system allows the user to generate homozygous modified cell clones by using the same homologous recombination vector with two different resistance genes against antibiotics for eukaryotic cells.

The materials and methods employed in these experiments are now described.

Materials and Methods

Figure 5:
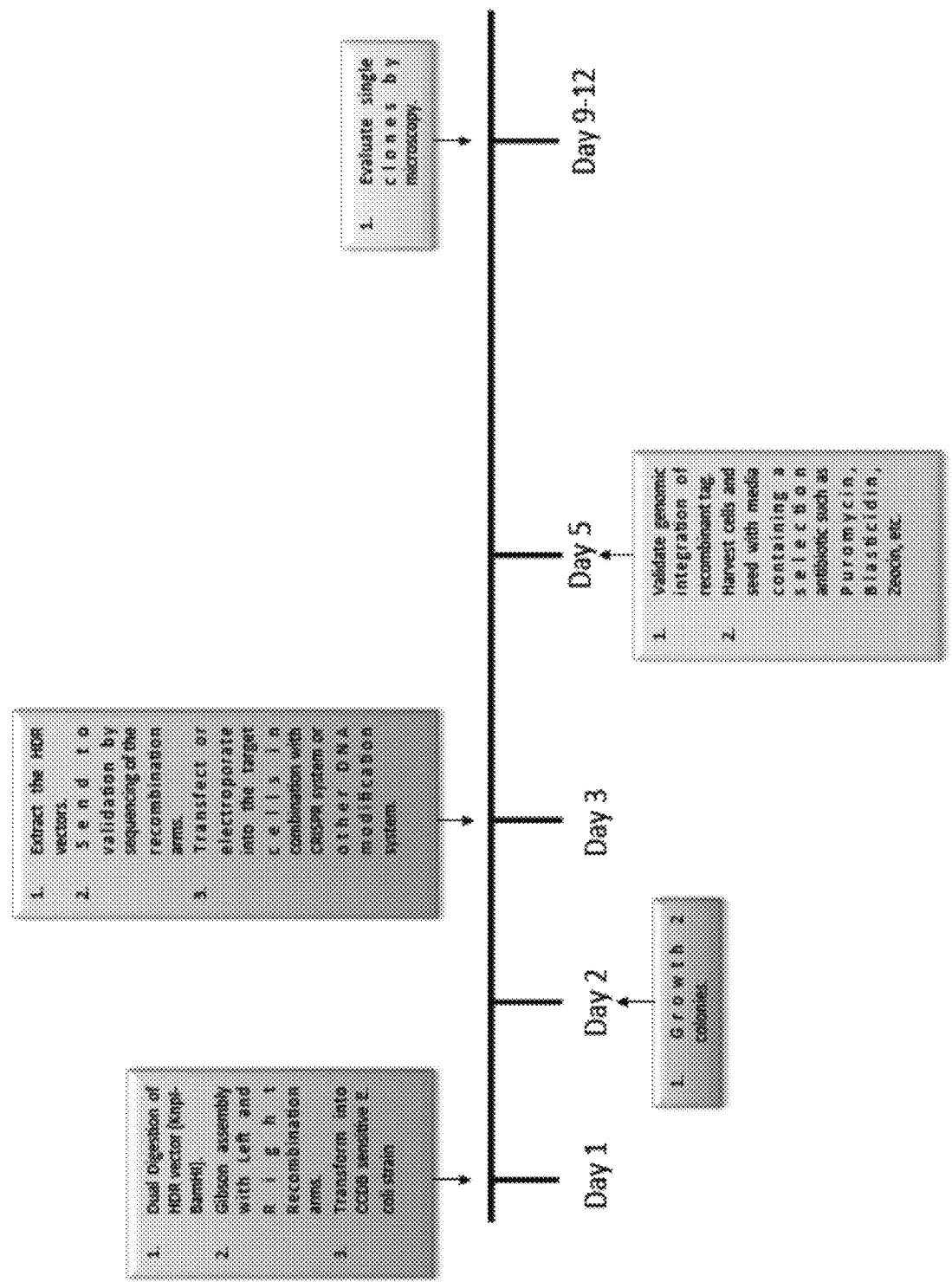
FIG. 5 depicts a protocol for developing homologous recombination vectors and selection of modified cell lines.

The selected backbone HDR donor vector (500 ng) was digested with KpnI and BamHI in a final volume of 20 uL. Synthetic left and right recombination arms were diluted in TE buffer at a final concentration of 25 ng/μL. A Gibson assembly reaction was performed by mixing 2 μL of the digested vector reaction, 1.5 μL of each recombination arm and 5 μL of NeBuilder master mix (New England Biolabs). The reaction mixture was incubated at 50° C. for 1 hour. 4 μL of the Gibson assembly reaction was transformed into a chemically competent E. coli strain sensitive to the CcdB gene (e.g. DH5α, JM109, STLB3, etc.). Cells were grown overnight at 35° C. Plasmids were extracted and the HDR recombination plasmids were verified by sequencing (FIG. 5).

The results of the experiments are now described.

Generation of a Cell Line with a Red Fluorescent Protein Tag for the Protein Histone 3.

A CRISPR expression vector was designed to express an sgRNA for cutting the last exon of the Histone 3 gene (gene symbol: H3F3B) in human cells.

Left and right recombination arms (~440-600 bp long) were selected next to the cut side and were created as double stranded synthetic DNA fragments in order to generate a vector to induce homologous recombination in the cut DNA and to promote an in-frame insertion of a red fluorescent protein (mRuby3) at the C-terminal end of the Histone 3 protein.

Figure 6:
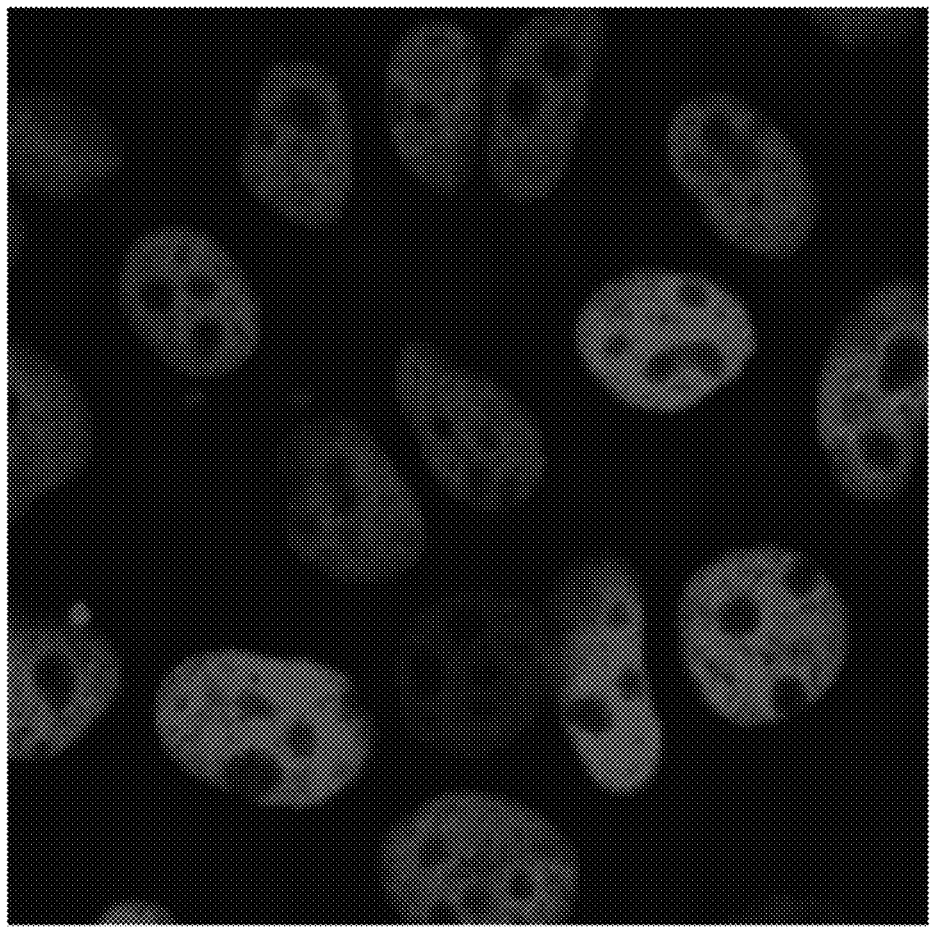
FIG. 6 depicts a representative image of a cell line with endogenous Histone 3 tagged with mRuby3 and selected with Zeocin™ (100 µg/ml).

The CRISPR vector and the Histone 3-mRuby3 HDR vector were cotransfected into HEK293T cells and the cells were evaluated 48 hours later for mRuby3 expression in the cell nucleus. The cells were harvested 72h after transfection and seeded with culture media containing a toxic antibiotic for eukaryotic cells (Zeocin™). The formation of positive colonies containing a red fluorescent nucleus was validated seven days after transfection (FIG. 6).

Generation of a Cell Line with a Red Fluorescent Protein Tag for the Protein Histone 3.

A CRISPR expression vector was designed to express an sgRNA for cutting the last exon of the Beta Tubulin gene (gene symbol: TUBB) in human cells.

Left and right recombination arms (~440-600 bp long) were selected next to the cut side and were created as double stranded synthetic DNA fragments in order to generate a vector to induce homologous recombination in the cut DNA and to promote an in-frame insertion of a green fluorescent protein (mClover3) at the C-terminal end of the Beta Tubulin protein.

Figure 7:
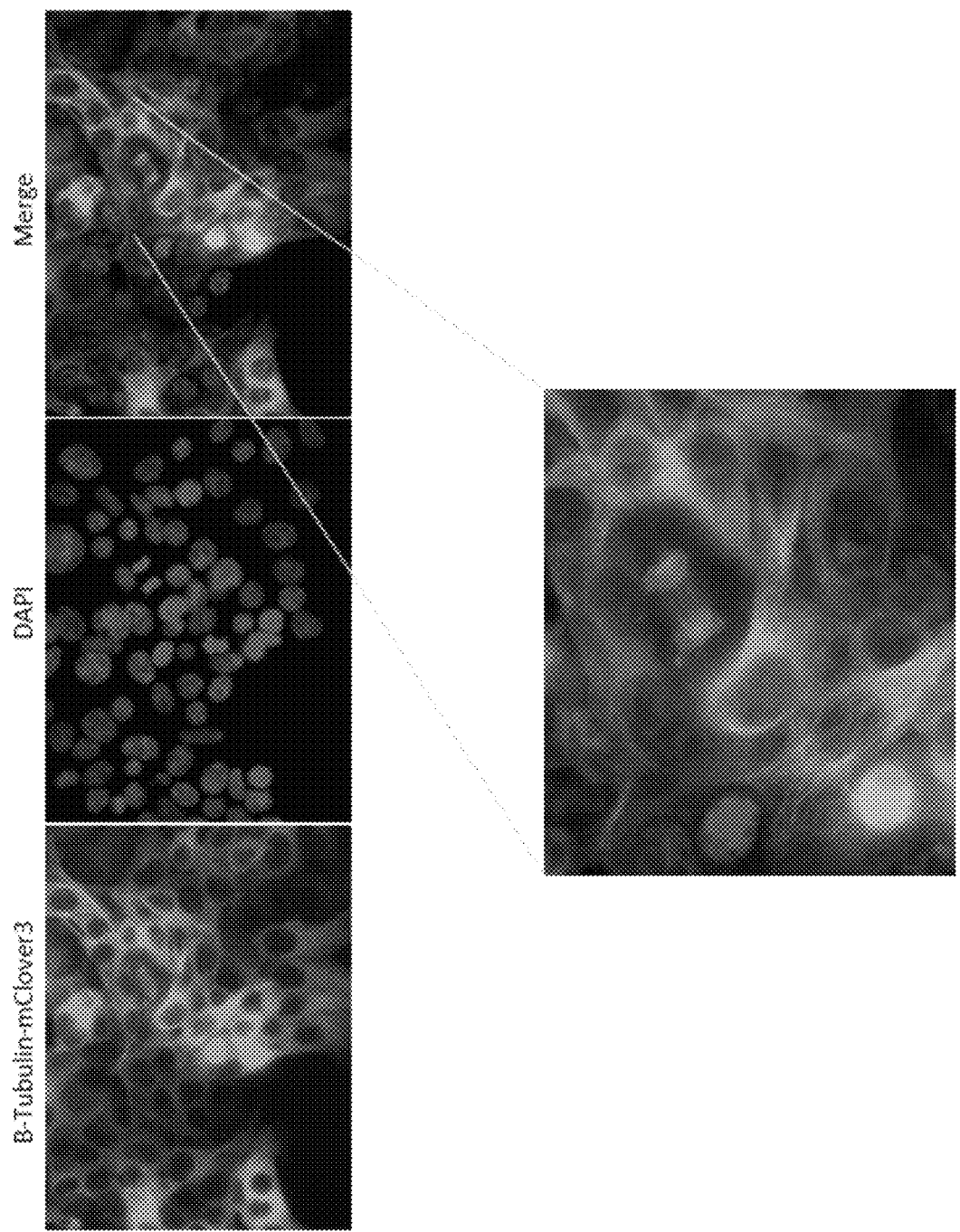
FIG. 7 depicts a representative image of a cell line with endogenous Beta Tubulin tagged with mClover3 and selected with puromycin (5 µM).

The CRISPR vector and the TUBB-Clover3 HDR vector were cotransfected into HEK293T cells and the cells were evaluated 48 hours later for mClover3 expression in the cells. The cells were harvested 72 hours after transfection and seeded with culture media containing a toxic antibiotic for eukaryotic cells (Puromycin). The formation of positive colonies containing a green fluorescent microtubules was validated seven days after transfection (FIG. 7).

Generation of a Dual Labeled Cell Line.

Figure 8:
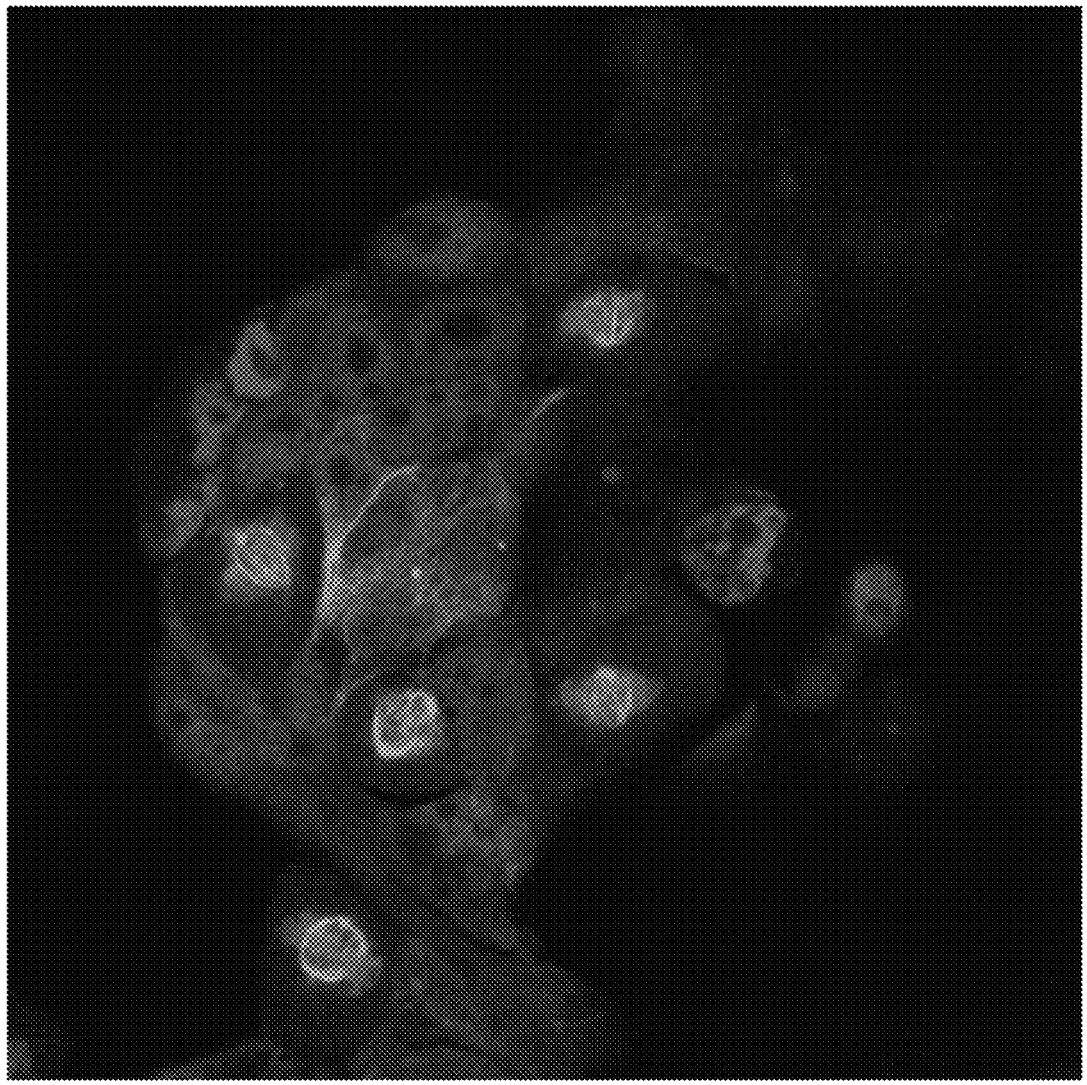
FIG. 8 depicts a cell line with multiplex labeling. The Endogenous Histone 3 was tagged with mRuby3 and Beta Tubulin was tagged with mClover3. Cells were selected with a mix of Zeocin™ and puromycin.

HEK293T cells that were previously modified to have a red fluorescent protein tag (mRuby3) in the Histone 3 protein were further modified to include an additional green fluorescent tag in the Beta tubulin gene. For this, the cells were cotransfected with a CRISPR plasmid targeting the last exon of the Beta Tubulin gene (gene symbol: TUBB) and a HDR vector to induce homologous recombination in the cut DNA and to promote an in-frame insertion of a green fluorescent protein (mClover3) at the C-terminal end of the Beta Tubulin protein. 48 hours later, mClover3 expression was evaluated in the cells. The cells were harvested 72h after transfection and seeded with culture media containing a toxic antibiotic for eukaryotic cells (Puromycin). The formation of positive colonies containing green fluorescent microtubules and red fluorescent Histone 3 in the nucleous was validated seven days after transfection (FIG. 8).

Generation of a Triple Labeled Cell Line.

Figures 9A, 9B, 9C:
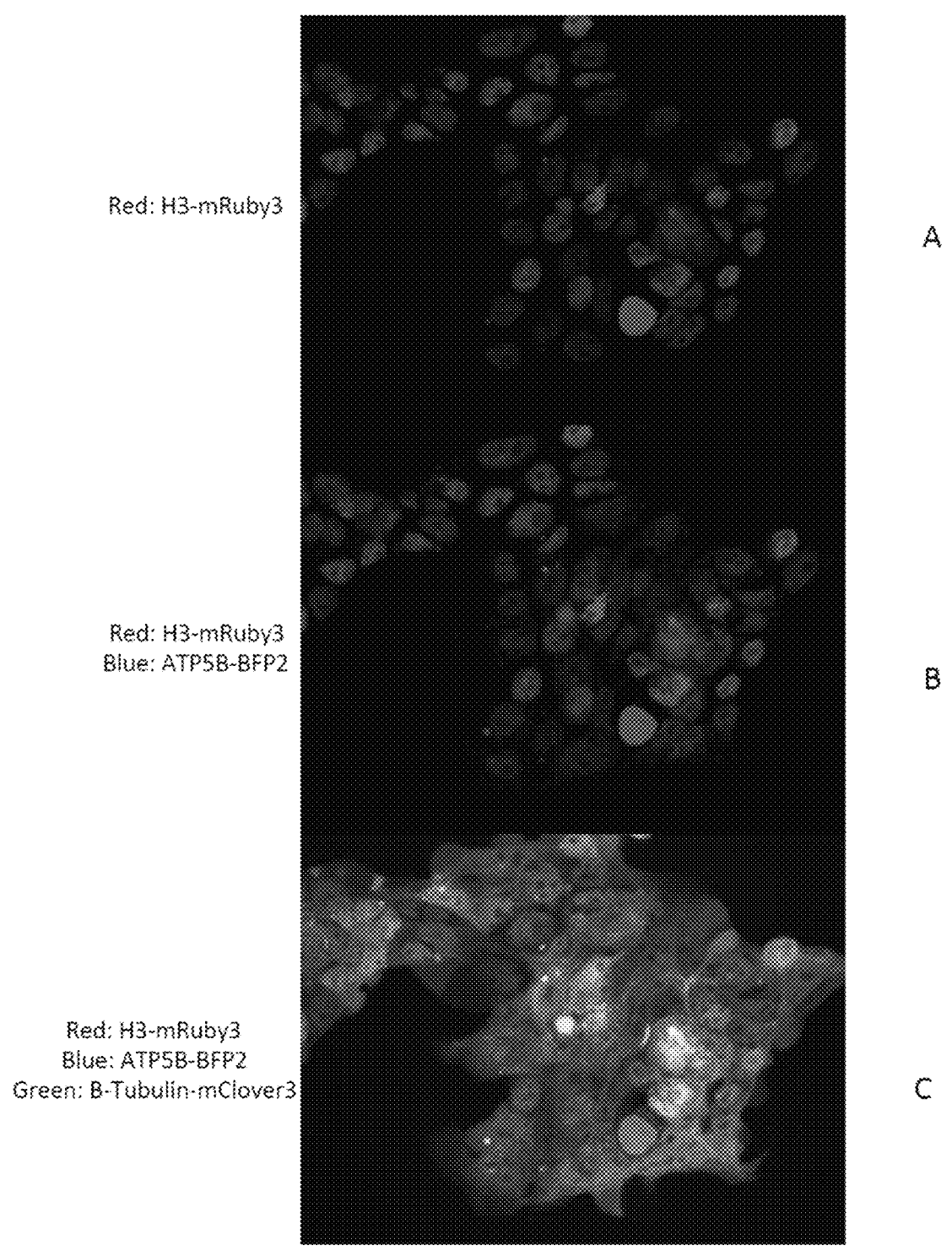

HEK293T cells that were previously modified to have a red fluorescent protein tag (mRuby3) in the Histone 3 protein and a green fluorescent protein (mClover3) tag in the Beta Tubulin protein were further modified to include an additional blue fluorescent tag in the mitochondrial protein Mitochondrial ATP Synthase Beta Subunit. For this, the cells were cotransfected with a CRISPR plasmid targeting the last exon of the Mitochondrial ATP Synthase Beta Subunit (gene symbol: ATP5B) and a HDR vector to induce homologous recombination in the cut DNA and to promote an in-frame insertion of a blue fluorescent protein (mTagBFP2) at the C-terminal end of the ATP synthase Beta subunit. The cells were evaluated for mTagBFP2 expression 48 hours later. The cells were harvested 72h after transfection and seeded with culture media containing a toxic antibiotic for eukaryotic cells (Blasticidin). The formation of positive colonies containing green fluorescent microtubules, red fluorescent Histone 3 in the nucleus and blue fluorescent mitochondria was validated seven days after transfection (FIG. 9)

Generation of a Cell Line with Heme Oxygenase 1 Tagged with NanoLuc® Luciferase.

Figure 10:
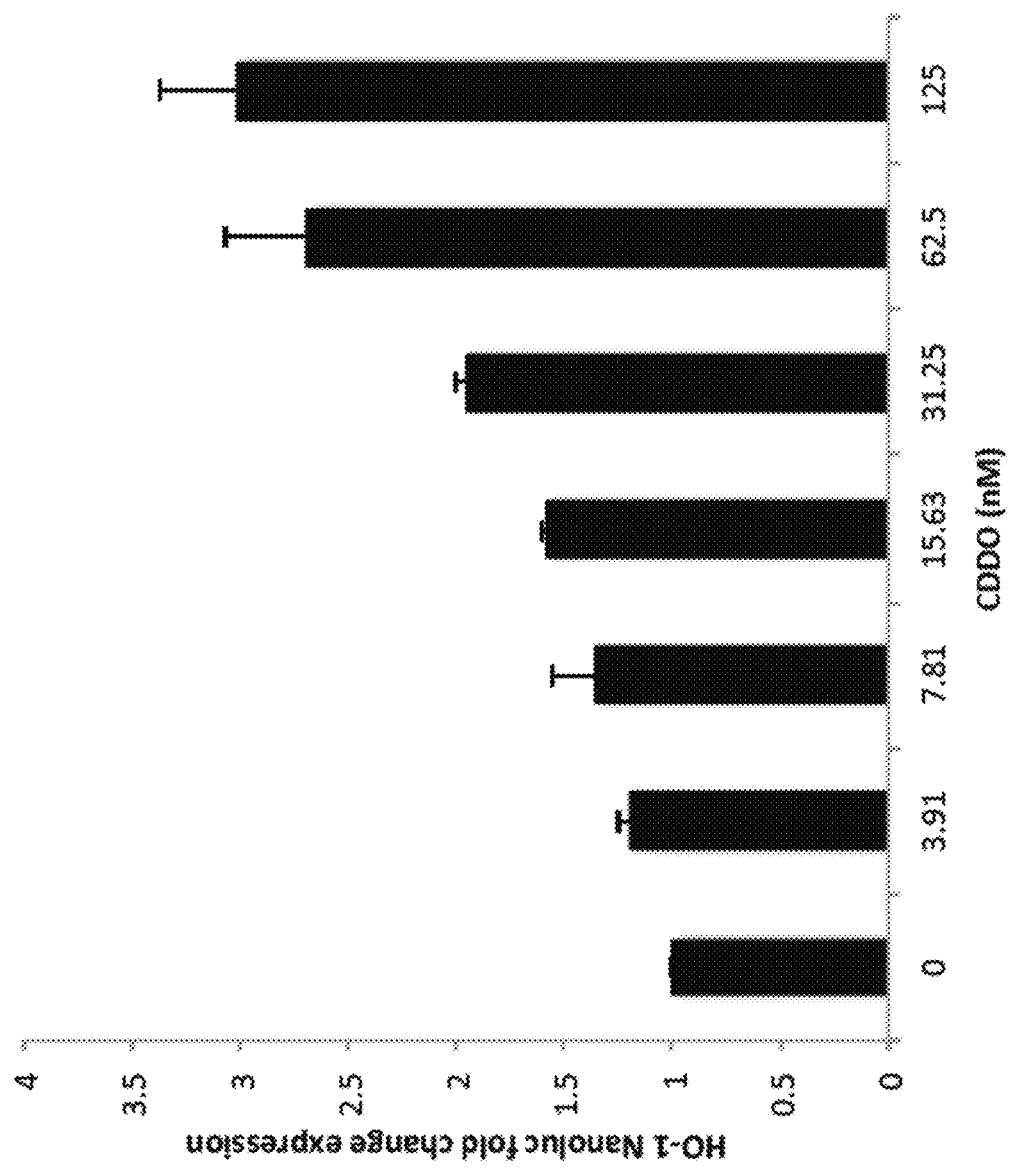
FIG. 10 depicts a cell line developed with Heme oxygenase I (HO-1) tagged with NanoLuc® luciferase. An HEK293T cell line was modified with the endogenous gene of HO-1 tagged with NanoLuc® luciferase. Changes in the expression of the HO-1 protein were measure after stimulation with a known activator of the expression of HO-1.
Figure 11:
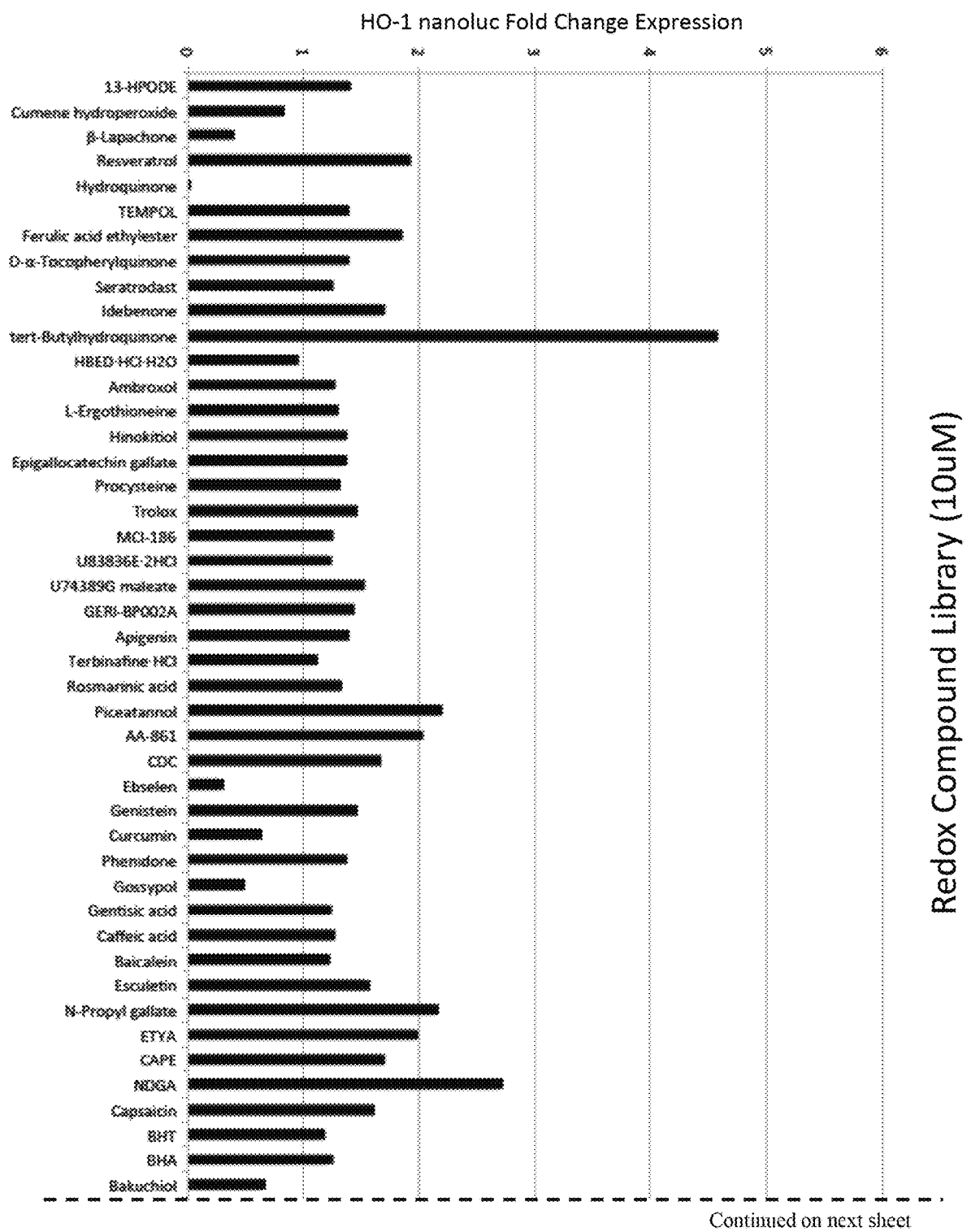
FIG. 11 depicts experimental results demonstrating the identification of potent inducers of HO-1 expression. The HO-1 NanoLuc® HEK293T cell line was used to evaluate changes in the expression of HO-1 after 16 hours of treatment with a library of 84 compounds with oxidant or antioxidant capacity.
Figure 11:
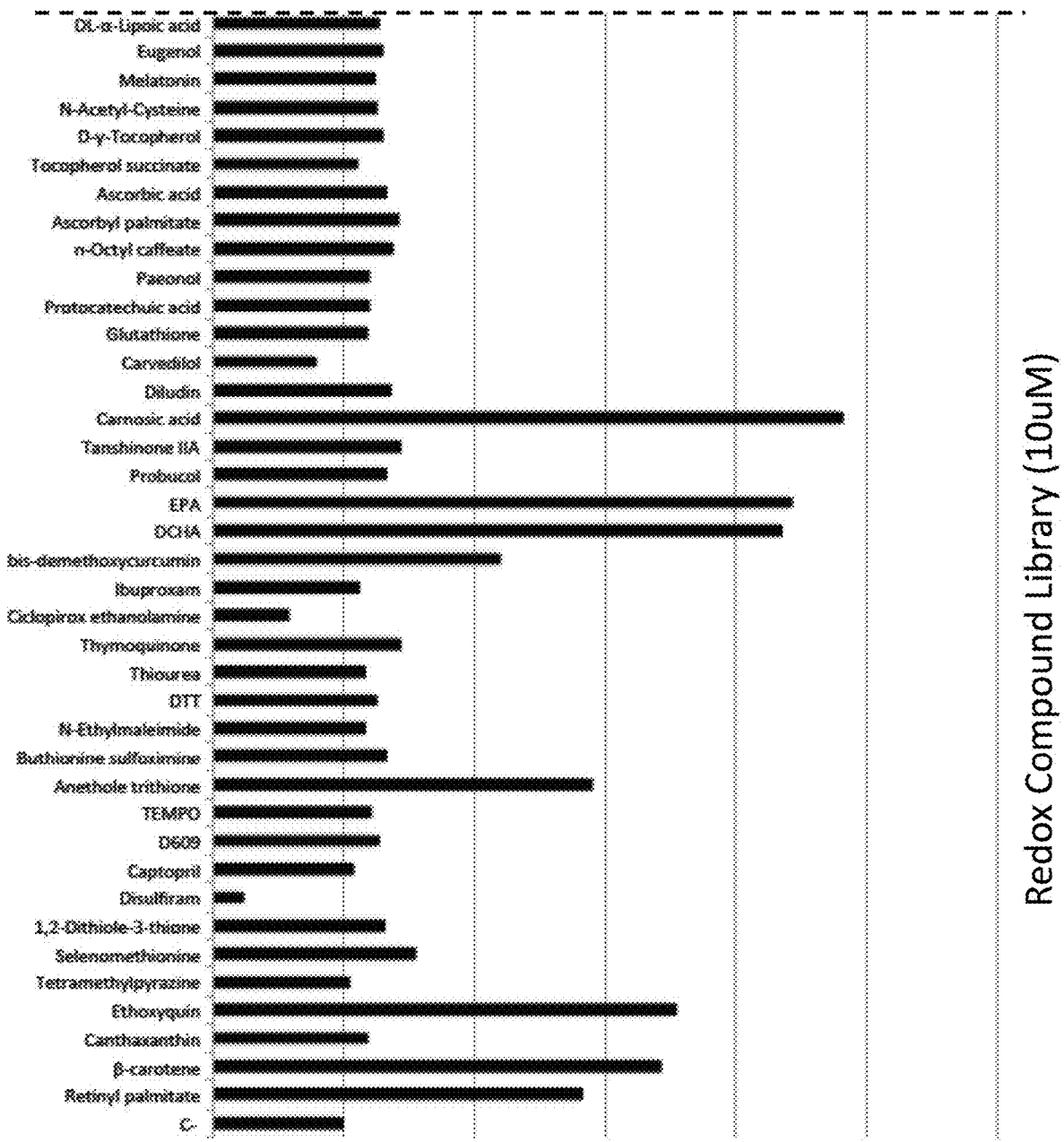
Figure 12:
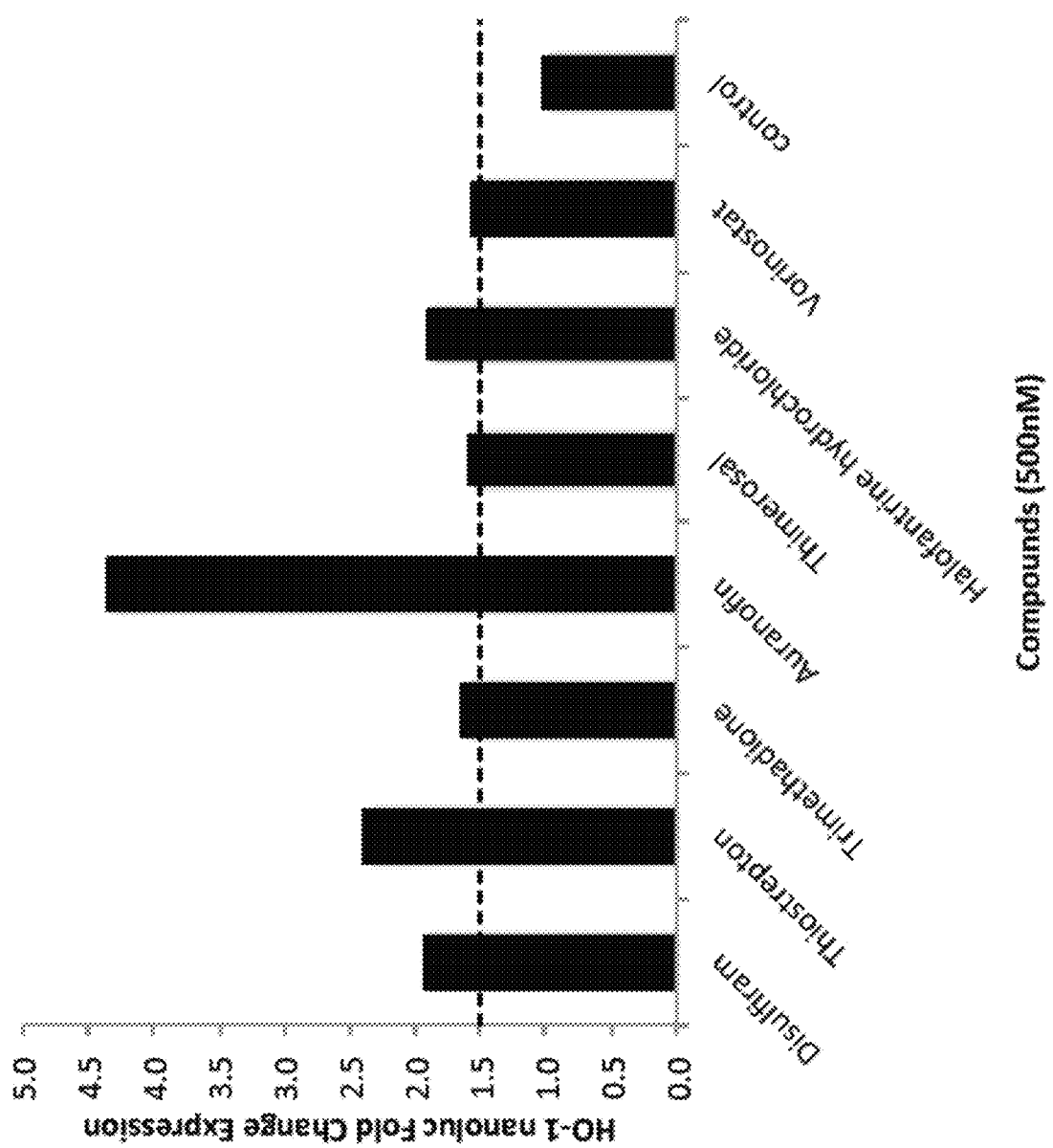
FIG. 12 depicts experimental results demonstrating the identification of FDA-approved drugs that activate the expression of HO-1. The HO-1 NanoLuc® HEK293T cell line was used to evaluate changes in the expression of HO-1 after 16 hours of treatment with a library of 1200 FDA-approved compounds. Seven compounds were able to increase the expression of HO-1 more than 1.5 Fold.

Heme oxygenase 1 (HO-1) is a gene target of the antioxidant response pathway. A modified cell line was generated to quickly quantify changes in the expression of the HO-1 by tagging the protein with NanoLuc® luciferase. For this, HEK293T cells were cotransfected with a CRISPR vector having a sgRNA sequence targeting the last exon of the HO-1 gene near the last codon and an HDR vector containing recombination arms (~630 bp) to induce DNA repair by homologous recombination. The HDR vector allow the in frame tagging of NanoLuc® luciferase and also contained a puromycin resistance gene under the control of an exogenous promoter (e.g. FIG. 3). After selecting pure clones with resistance to puromycin, the capacity of the new cell line to allow the quick detection of small changes in the expression of HO-1 after treating the cells with a known activator of HO-1 expression, the synthetic triterpenoid 2-cyano-3,12-dioxooleana-1,9(11)-dien-28-oic acid (CDDO), was verified (FIG. 10). The HO-1 NanoLuc® cell line was then used to screen a library of oxidant and antioxidant compounds and identify potent activators of HO-1 protein expression (FIG. 11). In addition, the HO-1 NanoLuc® cell line was used to screen a library of 1200 FDA-approved compounds and identify 7 compounds that are able to increase the protein expression of HO-1 (FIG. 12).

Example 2: Sequences of Fast-HDR Donor Plasmid Backbones

Fast-HDR donor plasmid backbone with linker peptide:

Underlined: KpnI (nucleotides 1-6 of SEQ ID NO:1 and nucleotides 682-687 of SEQ ID NO:1), EcoRI (nucleotides 700-705 of SEQ ID NO:1 and nucleotides 781-786 of SEQ ID NO:1), XbaI (nucleotides 853-858 of SEQ ID NO:1 and nucleotides 934-939 of SEQ ID NO:1), BamHI (nucleotides 1116-1121 of SEQ ID NO:1 and nucleotides 1797-1802 of SEQ ID NO:1); Italic: CCDB gene (nucleotides 336-641 of SEQ ID NO:1); Lower case: Linker (nucleotides 689-699 of SEQ ID NO:1); NNNNN: Insertion site 1 (e.g., for inserting a sequence encoding a tag, a marker, an exogenous gens, a fluorescent protein, a selectable marker, an antibiotic resistance gene and/or a purification tag) (nucleotides 706-780 of SEQ ID NO:1); Lower case italic: P2A peptide sequence (nucleotides 797-852 of SEQ ID NO:1); NNNNN: Insertion site 2 (e.g., for inserting a sequence encoding a tag, a marker, an exogenous gens, a fluorescent protein, a selectable marker, an antibiotic resistance gene and/or a purification tag) (nucleotides 859-933 of SEQ ID NO:1); Bold: mRNA Stabilization Sequence (nucleotides 942-1115 of SEQ ID NO:1); Italic: CCDB gene (nucleotides 1451-1756 of SEQ ID NO:1)

```
                                          (SEQ ID NO: 1)
GGTACCGGCTTACTAAAAGCCAGATAACAGTATGCGTATTTGCGCGCTGA

TTTTTGCGGTATAAGAATATATACTGATATGTATACCCGAAGTATGTCAA

AAAGAGGTGTGCTATGAAGCAGCGTATTACAGTGACAGTTGACAGCGACA

GCTATCAGTTGCTCAAGGCATATATGATGTCAATATCTCCGGTCTGGTAA

GCACAACCATGCAGAATGAAGCCCGTCGTCTGCGTGCCGAACGCTGGAAA

GCGGAAAATCAGGAAGGGATGGCTGAGGTCGCCCGGTTTATTGAAATGAA

CGGCTCTTTTGCTGACGAGAACAGGGACTGGTGAAATGCAGTTTAAGGTT

TACACCTATAAAAGAGAGAGCCGTTATCGTCTGTTTGTGGATGTACAGAG

TGATATTATTGACACGCCCGGGCGACGGATGGTGATCCCCCTGGCCAGTG

CACGTCTGCTGTCAGATAAAGTCTCCCGTGAACTTTACCCGGTGGTGCAT

ATCGGGGATGAAAGCTGGCGCATGATGACCACCGATATGGCCAGTGTGCC
```

-continued

*GGTCTCCGTTATCGGGGAAGAAGTGGCTGATCTCAGCCACCGCGAAAATG*

*ACATCAAAAACGCCATTAACCTGATGTTCTGGGGAATATAAATGTCAGGC*

*TCCGTTATACACAGCCAGTCTGCAGGTCGAC*<u>GGTACCC</u>aaggcggtgga<u>G</u>

<u>AATTCNNNNNNNNNNNNNNNNNNNNNNNNNNNNNNNNNNNNNNNNNNNNNN</u>

<u>NNNNNNNNNNNNNNNNNNNNNNNNNNNNNNNGAATTC</u>ggatctggagcaac aaacttctcactactcaaacaagcaggtgacgtggaggagaatcccgggc ct<u>TCTAGA</u>NNNNNNNNNNNNNNNNNNNNNNNNNNNNNNNNNNNNNNNNNNN NNNNNNNNNNNNNNNNNNNNNNNNNNNNNNNNN<u>TCTAGA</u>taaATTCGTCA

GTAGGGTTGTAAAGGTTTTTCTTTTCCTGAGAAAACAACCTTTTGTTTTC

TCAGGTTTTGCTTTTTGGCCTTTCCCTAGCTTTtAAAAAAAAAAAAGCAAA

AGACGCTGGTGGCTGGCACTCCTGGTTTCCAGGACGGGGTTCAAGTCCCT

GCGGTGTCTTTGCTT<u>GGATCC</u>GGCTTACTAAAAGCCAGATAACAGTATGC

*GTATTTGCGCGCTGATTTTTGCGGTATAAGAATATATACTGATATGTATA*

*CCCGAAGTATGTCAAAAAGAGGTGTGCTATGAAGCAGCGTATTACAGTGA*

*CAGTTGACAGCGACAGCTATCAGTTGCTCAAGGCATATATGATGTCAATA*

*TCTCCGGTCTGGTAAGCACAACCATGCAGAATGAAGCCCGTCGTCTGCGT*

*GCCGAACGCTGGAAAGCGGAAAATCAGGAAGGGATGGCTGAGGTCGCCCG*

*GTTTATTGAAATGAACGGCTCTTTTGCTGACGAGAACAGGGACTGGTGAA*

*ATGCAGTTTAAGGTTTACACCTATAAAAGAGAGAGCCGTTATCGTCTGTT*

*TGTGGATGTACAGAGTGATATTATTGACACGCCCGGGCGACGGATGGTGA*

*TCCCCCTGGCCAGTGCACGTCTGCTGTCAGATAAAGTCTCCCGTGAACTT*

*TACCCGGTGGTGCATATCGGGGATGAAAGCTGGCGCATGATGACCACCGA*

*TATGGCCAGTGTGCCGGTCTCCGTTATCGGGGAAGAAGTGGCTGATCTCA*

*GCCACCGCGAAAATGACATCAAAAACGCCATTAACCTGATGTTCTGGGA*

*ATATAAATGTCAGGCTCCGTTATACACAGCCAGTCTGCAGGTCGAC*<u>GGAT</u>

<u>CC</u>

Fast-HDR donor plasmid backbone with internal promoter:

Underlined: KpnI (nucleotides 1-6 of SEQ ID NO:2 and nucleotides 682-687 of SEQ ID NO:2), EcoRI (nucleotides 700-705 of SEQ ID NO:2 and nucleotides 756-761 of SEQ ID NO:2), AgeI (nucleotides 1303-1308 of SEQ ID NO:2), XbaI (nucleotides 1359-1364 of SEQ ID NO:2), BamHI (nucleotides 1541-1546 of SEQ ID NO:2 and nucleotides 2222-2227 of SEQ ID NO:2); Italic: CCDB gene (nucleotides 336-641 of SEQ ID NO:2); Lower case: Linker (nucleotides 689-699 of SEQ ID NO:2); NNNNN: Insertion site 1 (e.g., for inserting a sequence encoding a tag, a marker, an exogenous gens, a fluorescent protein, a selectable marker, an antibiotic resistance gene and/or a purification tag) (nucleotides 706-755 of SEQ ID NO:2); Bold underlined: EF1alpha promoter sequence (nucleotides 811-1293 of SEQ ID NO:2); NNNNNN: Insertion site 2 (e.g., for inserting a sequence encoding a tag, a marker, an exogenous gens, a fluorescent protein, a selectable marker, an antibiotic resistance gene and/or a purification tag) (nucleotides 1309-1358 of SEQ ID NO:2); Bold: mRNA Stabilization Sequence (nucleotides 1368-1540 of SEQ ID NO:2); Italic: CCDB gene (nucleotides 1876-2181 of SEQ ID NO:2)

(SEQ ID NO: 2)
<u>GGTACC</u>GGCTTACTAAAAGCCAGATAACAGTATGCGTATTTGCGCGCTGA

TTTTTGCGGTATAAGAATATATACTGATATGTATACCCGAAGTATGTCAA

AAAGAGGTGTGCTATGAAGCAGCGTATTACAGTGACAGTTGACAGCGACA

GCTATCAGTTGCTCAAGGCATATATGATGTCAATATCTCCGGTCTGGTAA

GCACAACCATGCAGAATGAAGCCCGTCGTCTGCGTGCCGAACGCTGGAAA

GCGGAAAATCAGGAAGGGATGGCTGAGGTCGCCCGGTTTATTGAAATGAA

CGGCTCTTTTGCTGACGAGAACAGGGACTGGTGAAATGCAGTTTAAGGTT

TACACCTATAAAAGAGAGAGCCGTTATCGTCTGTTTGTGGATGTACAGAG

TGATATTATTGACACGCCCGGGCGACGGATGGTGATCCCCCTGGCCAGTG

CACGTCTGCTGTCAGATAAAGTCTCCCGTGAACTTTACCCGGTGGTGCAT

ATCGGGGATGAAAGCTGGCGCATGATGACCACCGATATGGCCAGTGTGCC

GGTCTCCGTTATCGGGGAAGAAGTGGCTGATCTCAGCCACCGCGAAAATG

ACATCAAAAACGCCATTAACCTGATGTTCTGGGGAATATAAATGTCAGGC

TCCGTTATACACAGCCAGTCTGCAGGTCGAC<u>GGTACCC</u>aaggcggtgga<u>G</u>

<u>AATTC</u>NNNNNNNNNNNNNNNNNNNNNNNNNNNNNNNNNNNNNNNNNNNNN

NNNNN<u>GAATTC</u>AATAAAAGATCTTTATTTTCATTAGATCTGTGTGTTGGT

TTTTTGTGTTCGCTACAATATTTTCCTGAACGGAAGAATAAATAAAACT

TGTCCTGTAAAGAAAACCCAGGTAAAGGAAAGTGGCAGTCCAGACTGCCC

GGAAGTTCCTGGAGGCTAAGGCCTCACCCCCGTCGCTTGATAGGACCTGC

TGAGCCACATGACTAAGGCACGATCGCCTCCGCACGTGTAAAGGTGCTGG

GTTCCAAGATGGCTGCCCCGCCGCGAGGCCCGACTTAAGTATGTCACTTC

CGCACCAGCGAGAAAGGCGGACCCTTCAGCCAATGAGGCCATAGGGCGGG

GCTAGGCCATGATGGGCTTTCAAACTACCCAATAGGGCGTCCGAACTAAA

GCGCCTACAAAGTAACGTCACGTCGAGTTGCAGAGCGCCGGCAGGCGGGG

CAGAGGTGGCCAAGCCAATGCGATGGCTGGGGCGGGGTCGGACGCTCTAT

AAGTTGTCGATAGGCGGGCACTCCGCCCTAGATTCTAAGGACCGCCGCCA

CC<u>ACCGGT</u>NNNNNNNNNNNNNNNNNNNNNNNNNNNNNNNNNNNNNNNNNN

NNNNNNNN<u>TCTAGA</u>taaATTCGTCAGTAGGGTTGTAAAGGTTTTTCTTTT

CCTGAGAAAACAACCTTTTGTTTTCTCAGGTTTTGCTTTTTGGCCTTTCC

CTAGCTTTtAAAAAAAAAAAAGCAAAGACGCTGGTGGCTGGCACTCCTGG

TTTCCAGGACGGGGTTCAAGTCCCTGCGGTGTCTTTGCTT<u>GGATCC</u>GGCT

TACTAAAAGCCAGATAACAGTATGCGTATTTGCGCGCTGATTTTTGCGGT

ATAAGAATATATACTGATATGTATACCCGAAGTATGTCAAAAAGAGGTGT

GCTATGAAGCAGCGTATTACAGTGACAGTTGACAGCGACAGCTATCAGTT

GCTCAAGGCATATATGATGTCAATATCTCCGGTCTGGTAAGCACAACCAT

GCAGAATGAAGCCCGTCGTCTGCGTGCCGAACGCTGGAAAGCGGAAAATC

AGGAAGGGATGGCTGAGGTCGCCCGGTTTATTGAAATGAACGGCTCTTTT

GCTGACGAGAACAGGGACTGGTGAAATGCAGTTTAAGGTTTACACCTATA

AAAGAGAGAGCCGTTATCGTCTGTTTGTGGATGTACAGAGTGATATTATT

GACACGCCCGGGCGACGGATGGTGATCCCCCTGGCCAGTGCACGTCTGCT

-continued

```
GTCAGATAAAGTCTCCCGTGAACTTTACCCGGTGGTGCATATCGGGGATG

AAAGCTGGCGCATGATGACCACCGATATGGCCAGTGTGCCGGTCTCCGTT

ATCGGGGAAGAAGTGGCTGATCTCAGCCACCGCGAAAATGACATCAAAAA

CGCCATTAACCTGATGTTCTGGGGAATATAAATGTCAGGCTCCGTTATAC

ACAGCCAGTCTGCAGGTCGACGGATCC
```

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:
1. An HDR donor vector comprising a nucleic acid sequence selected from the group consisting of SEQ ID NO:1 and SEQ ID NO:2.

\* \* \* \* \*